(12) United States Patent
Timmons et al.

(10) Patent No.: US 6,306,506 B1
(45) Date of Patent: Oct. 23, 2001

(54) MOLECULAR TAILORING OF SURFACES

(75) Inventors: Richard B. Timmons; Jenn-Hann Wang, both of Arlington, TX (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 09/231,391

(22) Filed: Jan. 13, 1999

Related U.S. Application Data

(63) Continuation of application No. 08/632,935, filed on Apr. 16, 1996, now Pat. No. 5,876,753.
(51) Int. Cl.[7] .................................................... B32B 27/00
(52) U.S. Cl. .......................... 428/422; 428/421; 428/446
(58) Field of Search .................................. 428/421, 422, 428/447, 411.1, 446

(56) References Cited

U.S. PATENT DOCUMENTS

| | | | |
|---|---|---|---|
| 4,478,875 | * 10/1984 | Pachonik et al. | 427/41 |
| 4,839,207 | * 6/1989 | Yoshitomi et al. | 428/64 |
| 5,055,316 | 10/1991 | Hoffman et al. | 427/2 |
| 5,178,962 | 1/1993 | Miyamoto et al. | 428/463 |
| 5,217,492 | 6/1993 | Guire et al. | 623/11 |
| 5,258,127 | 11/1993 | Gsell et al. | 210/767 |
| 5,342,693 | 8/1994 | Winters et al. | 428/447 |
| 5,451,428 | 9/1995 | Rupp | 427/2.12 |
| 5,451,459 | * 9/1995 | Ogawa et al. | 428/333 |
| 5,695,836 | * 12/1997 | Ogawa et al. | 428/34.6 |

OTHER PUBLICATIONS

Clark, "Plasma Polymerization. III. An ESCA Investigation of Polymers Synthesized by Excitation of Inductively Coupled RF Plasmas in Perfluorocyclohexa–1,3–and1, 4–Diens, and in Perfluorocyclohexene", *Journal of Polymer Science.*, 18:407–425, 1980.

Clemence et al., "Photoimmobilization of a Bioactive Laminin Fragment and Pattern–Guided Selective Neuronal Cell Attachment", *BioconjugateChem.*, 6:411–417, 1995.

(List continued on next page.)

*Primary Examiner*—D. S. Nakarani
(74) *Attorney, Agent, or Firm*—Jackson Walker L.L.P.

(57) ABSTRACT

This invention describes a new approach to three-dimensional molecular tailoring of surfaces. In this process, a plasma deposition step is initially employed to deposit reactive functional groups on the surface of a solid substrate. This is then followed by immersion of the coated substrate in a solution during which time solute molecules react with the functional surface groups introduced during the plasma process. Solute molecules are attached to the surface during this second step. This simple two-step process is of general utility in that both the nature of the plasma introduced surface group and the nature of the solute molecules can be varied. Additionally it is possible to provide exact control of the surface density of reactive groups introduced during the plasma process and thus the concentration of solute molecules coupled to the solid surfaces. A particularly significant aspect of this invention is that the second step chemical derivatization reactions can be carried out using aqueous solutions at room temperature. The RF plasma polymerization of substituted perfluorohexenes is shown to produce films having unusually high —$CF_3$ content. These films are produced under both pulsed and continuous-wave plasma deposition conditions. The relative —$CF_3$ content of these polymers increases with decreasing average RF power absorbed during the film formation processes. The films produced under the least energetic condition (i.e., pulsed plasma, 0.1 ms on/3.0 ms off and 100 watts peak power) are exceptionally hydrophobic, exhibiting advancing and receding water contact angles in excess of those observed with Teflon® surfaces. The most hydrophobic films have a —$CF_3$ content which represents 40% of the carbon atoms present in the sample.

4 Claims, 16 Drawing Sheets

OTHER PUBLICATIONS

Massia and Hubbell, "Human Endothelial Cell Interactions with Surface–Coupled Adhesion Peptides on a Nonadhesive Glass Substrate and Two Polymeric Biomaterials", *Journal of Biomedical Materials Research*, 25:223–242, 1991.

Panchalingam, et al., "Molecular surface tailoring of biomaterials via pulsed RF plasma discharges", *J. biomater. Sci. Polymer Edn.* 5(1/2) pp. 131–145, 1993.

Panchalingem, et al., "Molecular Tailoring of Surfaces Via Pulsed RF Plasma Depositions", *Journal of Applied Polymer Science*, 54:123–141, 1994.

Ranieri, et al.. "Spatial Control of Neuronal Cell Attachment and Differentiation on Covantly Patterned Laminin Oligopeptide Substrates", *Int. J. Devl Neuroscience*, 12(8):725–735, 1994.

Savage, "Molecular Control Of Surface Film Compositions Via Pulsed Radio–Frequency Plasma Depositon of PerfluoropropyleneOxide", Chem Mater. 3:575–577, 1991.

Sigrist, et al. "Surface Immobilization of Biomolecules By Light", *Optical Engineering*, 34(8):2339, 1995.

Yasuda, "Plasma Polymerization", P.2 Academic Press. NY, Copyright 1985, Academic Press, Inc.

International Search Report dated Jul. 31, 1997 (UTFL048P).

* cited by examiner (B) PET----->Allyl Bromide ---->YIGSR
(3/45 ms, 200w)   (pH=8.0, 23 C,  24 hrs)

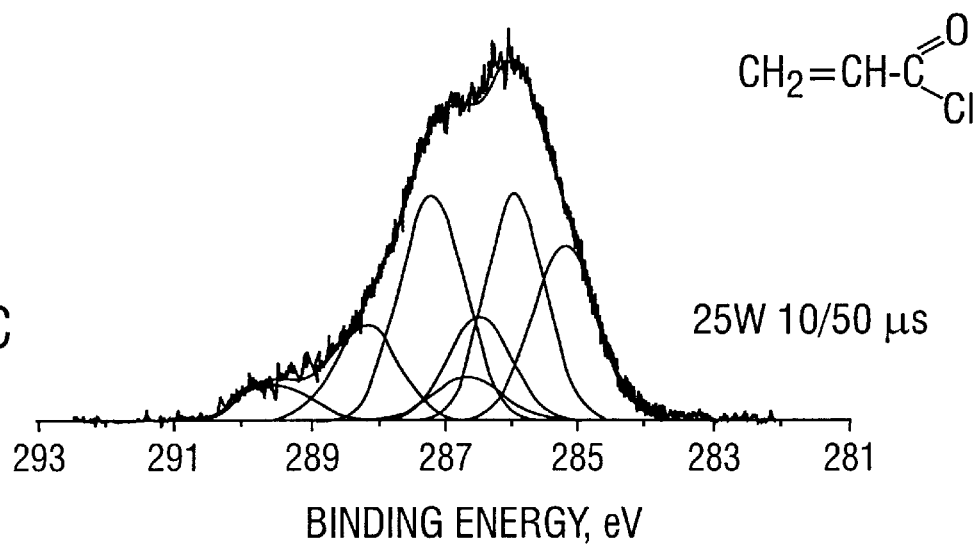
FIG. 8C  25W 10/50 μs
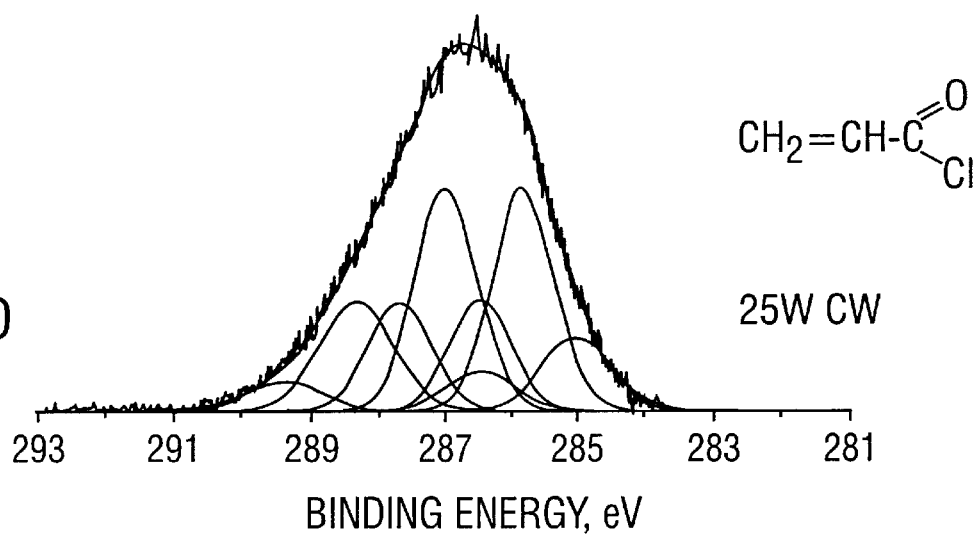
FIG. 8D  25W CW

MOLECULAR TAILORING OF SURFACES

This is a continuation of application Ser. No. 08/632,935 filed Apr. 16, 1996, now U.S. Pat. No. 5,876,753. +gi The U.S. Government has certain rights in the present invention pursuant to the National Institutes of Health under Grant #R01AR43186-01 and by the Texas Higher Education Coordinating Board ATP Program under Grant #003656-105.

FIELD OF THE INVENTION

This invention provides a new approach to molecular tailoring of surfaces.

BACKGROUND OF THE INVENTION

The chemical composition of surfaces plays a pivotal role in dictating the overall efficacy of many devices. Applications in which surface chemistry exerts a major influence in device performance include the biocompatibility of materials, biosensors, heterogeneous catalysis, and the permselectivity of membranes, to mention but a few of the many such examples. In recognition of the important role exerted by surfaces, surface modification research has represented an exceedingly active area for many years. A wide range of techniques, involving both physically and chemically oriented approaches, has been developed in efforts to provide specific improvements of surfaces. Examples of such work include various vapor deposition methods, plasma processes, sputtering techniques, chemical etching processes, ion implantation, etc. In these processes, the surface treatments are designed to improve device performance and/or reduce costs involved in preparation of substrate surfaces. An enormous patent literature exists describing the various surface modification techniques which have been developed and the many applications which have been identified.

Despite the extensive work in this area, a significant need remains for improved methods to control surface modification processes at the molecular level. Unfortunately, the majority of currently employed surface modification techniques provide unsatisfactory controllability of the film chemistry during the deposition process. Additionally, current surface modification techniques, as employed on industrial scale operations, are restricted to planar, 2-dimensional surface layers.

In recognition of the need for improved molecular level film chemistry control, and particularly the requirement for three-dimensionally molecularly designed surfaces, additional approaches to surface modification have been described in recent literature. For example, the use of self-assembling monolayers (SAM's) have been extensively developed during recent years to provide layered structures having three-dimensional molecular properties. A second developing approach to surface modifications, and one of direct relevance with respect to the present invention, is use of an initial surface treatment to introduce reactive functional groups which are then subjected to subsequent chemical derivatization processes. These multi-step procedures, ultimately resulting in coupling of specific molecules to the surface, can provide what may be described as three-dimensional molecularly tailored surface.

Although these new surface modification procedures have produced some interesting results, the overall processes described to date are exceedingly time-consuming, inefficient and require the use of undesirable hazardous solvents. Descriptions of recent literature reports of these surface modification processes clearly reveal the complex procedures involved in attempting to couple specific molecules to surfaces. For example, recent work has employed a plasma deposition method for introduction of surface hydroxyl (—OH) groups, which are then reacted in a second step to provide covalently bonded molecules tethered to the surface (Ranieri et al.). In this process, the plasma-introduced surface —OH groups are first reacted with di-imidazole, with this reaction being carried out in dry tetrahydrofuran at room temperature for 30 minutes. This was then followed by an aqueous solution reaction at 4° C. for 72 hours at a pH of 8.4 to covalently attach low molecular weight peptides to the surface. This process requires both the use of an nonaqueous solvent and an extraordinarily long (i.e., 72-hour) coupling reaction to couple the desired molecules to the surface (Ranieri et al.).

Alternately, a chemical process can be employed to introduce the surface hydroxyl groups which are then subsequently derivatized. For example, a complex procedure has been employed to provide a so-called glycol phase surface which contains reactive —OH groups (Massia et al.). In this procedure, glass coverslips are initially soaked in 0.5 M NaOH for 2 hours, then rinsed in deionized water and then immersed in pH 5.5 aqueous solution of (3-glycidoxypropyl)trimethoxy-silane. This reaction was maintained for 2 hours after which time the pH was adjusted to 3.0 followed by heating again for 1 hour to convert the oxirane moieties on the derivatized glass to glycol groups. This was followed by reaction of the surface hydroxyls with tresyl chloride using an acetone solvent followed by rinsing with 1 mM HCl and immersion in 0.2 M $NaHCO_3$ buffer at pH 9. Coupling of the desired peptides to the glass surface was then carried out via a 20-hour incubation reaction to the sulfonyl-containing surfaces.

Still other workers have employed a somewhat different but equally complex route to obtain the glycophase glass surface (Clemence et al.). In this work, they employ a sequence in which the glass coverslips are incubated for 5 minutes in a boiling solution of $NH_3/H_2O_2/H_2O$. After rinsing with distilled water, the glass disks were rinsed in acetone after which they were reacted with a solution containing CPTMS and TEA in dry toluene. This was followed by successive washes in chloroform, acetone and methanol and then dried in vacuum. This was followed by a HCl rinse, then incubation for 60 min. at 90° C. in 1 mM HCl followed by rinsing with doubly distilled water to obtain the glycophase glass. These workers then employed a photochemical method to attach peptides covalently to the hydroxylated surfaces. This technique requires the initial coupling of a photochemical label to the peptides. The photochemical labels employed were N-{m-[3-(trifluoromethyl)-diazirin-3-yl]phenyl}-4-maleimidobutyramide or 4-maleimidobenzophenone. With either label a complicated reaction procedure is required to attach them to the peptide with the synthesis requiring the use of HPLC to separate the desired complex from the reaction mixtures. These photolabeled molecules are then subsequently attached to hydroxylated surfaces using a photochemical technique.

Alternately, biomolecule surface immobilization has been reported using bifunctional photochemical sensitive molecules to achieve this goal (Sigrist et al.). In this approach, a heterobifunctional crosslinker is employed to link the biomolecules to a surface. For example, 3-(trifluoromethyl)-3-(m-isothiocyanophenyl) diazirine is initially coupled to a surface containing amine groups via coupling through the isothiocyano group. Subsequent photolysis of the surface attached diazirine generates a carbene radical which can react with biomolecules, if the biomolecules are within molecular vicinity at the time of carbene generation. As noted by these authors: "If target molecules are not present during the carbene lifetime, the intermediate will react with every molecular species present including water." This of course leads to relatively low surface immobilization of the protein molecules as the process selectivity is relatively low. Thus this recent biomolecule surface immobilization process requires synthesis of a complex heterobifunctional photochemical sensitive intermediate linker molecule, attachment of this linker to a functionalized surface and, finally, photochemical attachment of this linker to the biomolecules. Over all the process is complex and it results in relatively low yields and low selectivity of biomolecule attachment to surfaces.

The above results have been cited to document the relatively complex reaction procedures currently being employed to covalently attach molecules to surfaces. The research cited above is from leading researchers and includes literature citations as recent as 1995. Thus it seems accurate to conclude that the complex techniques employed represent "state-of-the-art" in surface modifications in which molecules are attached to activated surfaces.

The process of the present invention is to be contrasted with numerous earlier applications of plasma surface modifications to enhance the interaction of solid substrates with other molecules and materials. Earlier plasma depositions were employed to improve the adsorption and/or adhesion of various molecules to the modified surfaces. For example, U.S. Pat. Nos.5,055,316 (Hoffman et al.) and 5,258,127 (Gsell et al.) both employed plasma surface modification to enhance adsorption of various biomolecules. In a similar vein, U.S. Pat. No. 5,178,962 (Miyamoto et al.) utilized a plasma discharge process to change the chemistry of a macromolecular synthetic resin film by exposure to excited plasma species to generate surface active groups, which are then coupled to metal atoms to form a metallic outer layer. This latter work involved non-polymerizable gases and the metal films were deposited on the plasma activated surfaces by high energy vapor deposition processes.

One way that the present invention differs from the above noted techniques in that the initial plasma surface modification step is directly followed by a chemical derivatization process in which desired molecules are covalently bound to the surfaces via simple chemical reaction.

SUMMARY OF THE INVENTION

The present invention focuses upon a process for preparing a solid surface attached to a target material. The process includes fixing a carbonaceous compound having a reactive functional group to a surface by low power plasma deposition. As used herein, the term "carbonaceous compound" means an organic compound comprising carbon. Such low power plasma deposition permits retention of functional group activity. A target material may then be added directly to the activated surface by reaction with the reactive functional group, preferably in a single step. This results in a target material covalently bonded to the carbonaceous compound affixed by plasma deposition to the solid surface. The reacting step for coupling the target molecule is preferably a reaction carried out with a solution of target material. The solvent for the solution of target material is preferably water. Affixing of the carbonaceous compound having a reactive functional group is carried out by low power plasma deposition, most preferably a variable duty cycle pulsed plasma deposition with higher powers being utilized for initial depositions on the surface. Such variable duty cycles permit the deposition of carbonaceous compounds with reactive functional groups that control concentration. The reactive functional groups of the carbonaceous compounds include carbon-halogen, acid halide, acid anhydride, sulfhydryl, phosphide, carboxylic acid, aldehyde and ketone, for example, although others may be utilized as well. The halide is preferably chloride and the halogen is preferably bromine or iodine although chlorine may be used.

The substrates utilized may be any solid surface including polymer, ceramic, metal, silanized metal, carbon, fabric, glass, silanized glass, semiconductor, wood, rubber, paper, hydrogel, cellulose or composite. The solid substrates also include films, particularly polymeric films such as polysilicones, polyolefins, and many others too numerous to list.

Another important aspect of the present invention is the plasma deposition of a hydrophobic and substantially —$CF_3$ dominated perfluoro compound film. The preferred perfluoro compound is a perfluorocarbon such as the most preferred perfluorinated trifluoromethyl substituted perfluorohexene. To form a perfluorinated surface also having a reactive surface, a perfluorinated compound is mixed with a carbonaceous compound having a reactive functional group such as an akenyl or alkyl halide, isothiocyanate, cyanide, benzene, acetate, mercaptan, glycidyl ether, ether, chloroformate, methyl sulfide, phenyl sulfone, phosphonic dichloride, trimethylsilane, triethoxysilane, acid, acid halide, amine, alcohol, or phosphide. The target materials may include any substance capable of reacting with the reactive functional groups. Preferred target materials include amino acids, fluorinated amino acids, proteins, peptides, saccharides, hormones, hormone receptors, polynucleotides, oligonucleotides, carbohydrates, glycosaminoglycans (such as heparin, for example) polyethylene glycol and polyethylene oxide. Derivatives of all these various target materials may be prepared and still retain reactivity with one or more of the active functional groups such that they may be attached to an activated surface. In one aspect the present invention involves producing a surface with reduced adherence for biological materials. Surfaces with coupled polyethylene glycol, polyethylene oxide or abundant —$CF_3$ groups are among the most preferred substituents for producing a surface with reduced adherence for biological material. Since biological materials may be any of the components of circulating blood, particularly its protein and cellular components, although conceivably antibacterial or antimarine organism materials could be added as well. The present invention concerns the first production of a solid surface having a pendant bromoalkenyl, acid chloride or carboxylic acid group suitable for coupling to a target material. For purposes of perfluorinated surfaces, the present invention includes a solid surface having pendant perfluorinated groups where the carbon in $CF_3$ represents more than about 40% of the carbon present on the surface. A surface has been produced having a pendant perfluorinated carbonaceous compound with a water contact angle greater than about 120°.

BRIEF DESCRIPTION OF THE DRAWINGS

FIGS. 8A–8D show a high resolution C(1s) spectra of silicon surface substrates with acryloyl chloride deposits at various radiofrequency duty cycles.

DESCRIPTION OF PREFERRED EMBODIMENTS

Figure 1A:
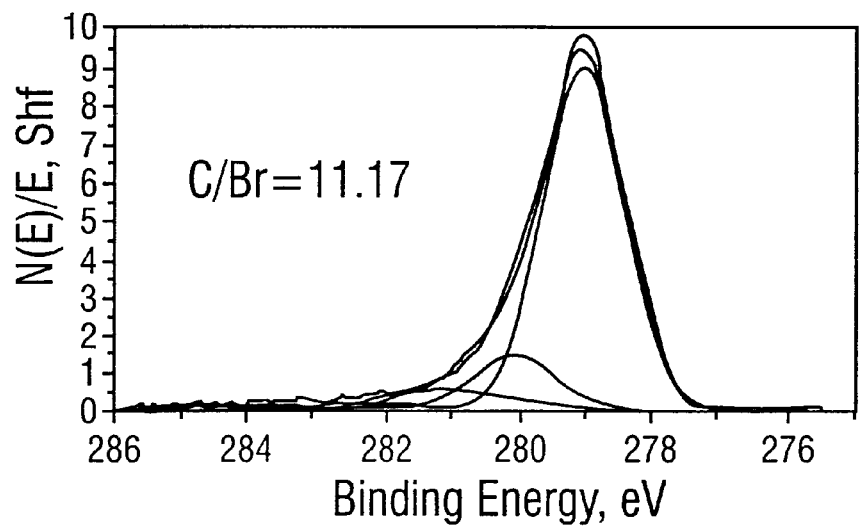
FIGS. 1A–1D shows high resolution C(1s) X-ray photoelectron spectra (XPS) of plasma polymerized films from allyl bromide monomer during continuous wave (CW) and pulsed plasma deposition.
Figure 1B:
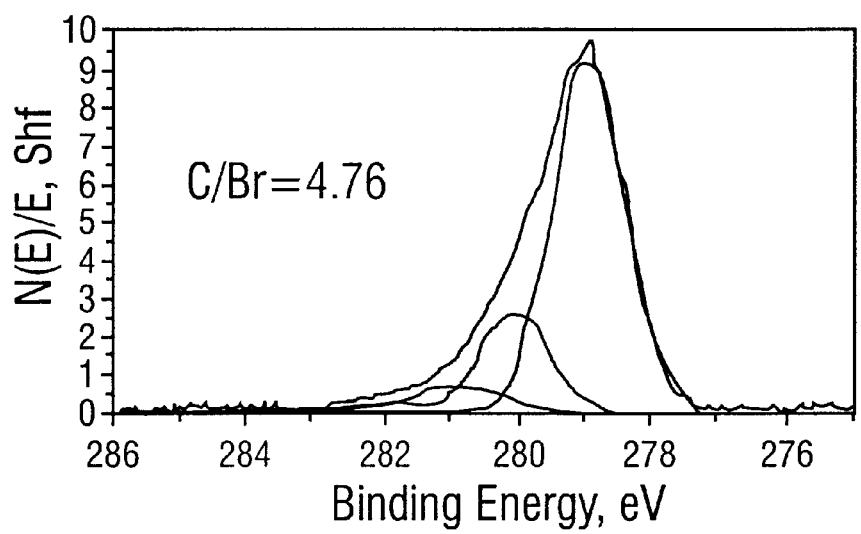
Figure 1C:
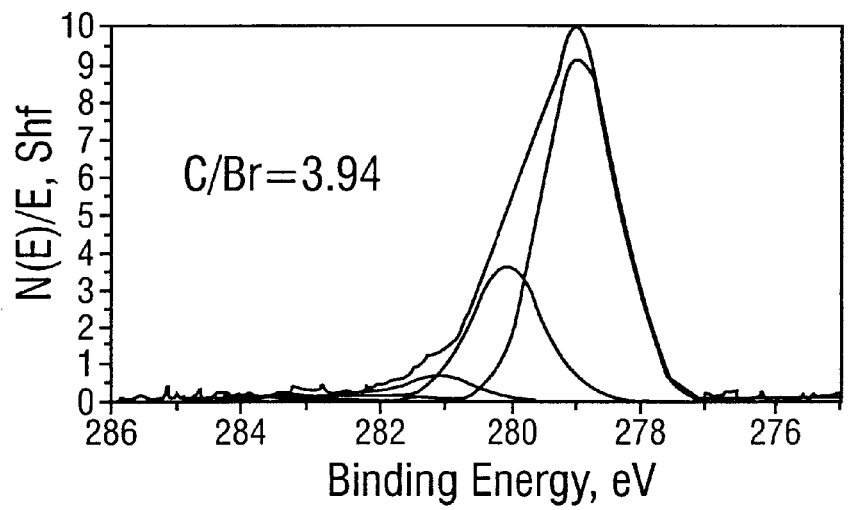
Figure 1D:
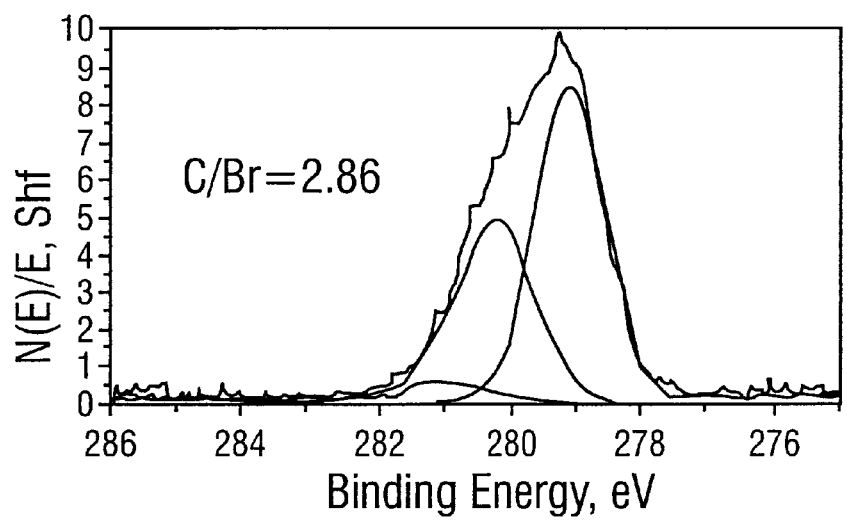

The present invention provides a significantly simpler and more versatile approach to surface modification science to provide three-dimensional molecular tailoring of solid substrates. This invention involves a simple, two-step procedure which allows for excellent controllability of the surface density of the molecules tethered to a surface. This new procedure significantly reduces the time requirement for surface tailoring and also eliminates the use of any hazardous solvents. Thus, it provides the first approach to molecular tailoring of surfaces which is useful in terms of large-scale, industrial type, applications.

Synthesis of a novel new fluorocarbon film is enabled. This film is obtained by plasma polymerization of a trimer mixture of substituted perfluorohexenes ($C_9F_{18}$) or the like. Use of low duty cycle pulsed or low energy continuous-wave plasmas provides films in which —$CF_3$ groups are the dominant functional group present. These —$CF_3$ rich films are exceptionally hydrophobic as revealed by water contract angle measurements.

As in some of the previously noted work, the first step in the present new surface modification process involves an initial plasma treatment. However, an important distinction between the present invention and techniques of previous workers, is that the present invention involves deposition of surface functional groups having significantly more chemical reactivity than those employed by previous workers. For example, the prior art noted earlier (Ranieri et al.; Massia et al; Clemence et al.) involved introduction of surface —OH groups which required complex and energetic reactions for attachment of intermediate molecules for subsequent attachment to biomolecules. On the other hand other groups (Sigrist et al.) employ —$NH_2$ functionalized surfaces which, as noted earlier, also requires complex procedures to achieve biomolecule surface attachment. Neither the —OH or —$NH_2$ surface groups possess the degree of reactivity towards other reactants, particularly nucleophiles, for example, as the surface active groups (e.g., C—Br, C—COCl, C—I, C—SH, C—COOH, etc.) of the present invention. Additionally, the present invention is able to provide unusual film chemistry controllability during the initial plasma deposition step which permits control of both the nature and surface density of the functional groups obtained from a given monomer. By introducing chemically more reactive functional groups than heretofore reported, molecules may be covalently coupled to these functionalized surfaces using unusually mild reaction conditions and short reaction times.

Important principles involved in the present invention can be illustrated with reference to a specific surface modification. In this process, a low pressure pulsed plasma polymerization is initially carried out using allyl bromide as the reactant monomer to deposit thin films on targeted substrates. By varying the duty cycle it is possible to control the bromine to carbon atom ratio in these films to a very exact degree. High resolution C(1s) electron spectra (XPS) were used to analyze plasma polymerized films obtained from allyl bromide monomer during continuous wave (CW) and pulsed plasma deposition runs using 200 watts power. The pulsed plasma depositions were carried out at, e.g., on-off duty cycles of 3/5, 3/15, 3/45 and 3/60 ms. There was a sharp increase in the bromine content of the film as the duty cycle during deposition is decreased. For example, an approximate 400% increase in the film content of bromine atoms, relative to the carbon atoms, is observed in comparing the pulsed run at the 3/60 ms duty cycle to the CW result.

The carbon-bromine bonds and other active functional groups introduced by the plasma surface treatment have a reactivity which permits ready covalent attachment of molecules to these surfaces via facile one-step processes. Furthermore these derivatization processes may be carried out in aqueous solution, at room temperature and with relatively short reaction times. A variety of nucleophilic displacement reactions have been carried out in which various molecules have been covalently bonded to the surface via displacement of, for example, the bromine atoms. An example of this reaction is shown for surface attachment of an amino acid via the reaction:

Surface-C—Br+$NH_2CH_2CH_2COOH$→Surface-C—NH—$CH_2CH_2COOH$+HBr     (1)

Similar type reactions can be carried out for a wide range of nucleophiles or coupling agents. Thus, as illustrated above, it is possible to avoid the complex chemistry of current molecular tailoring practices via introduction of more active surface functional groups.

The C—Br groups mentioned in this illustration represent but one of a range of reactive surface groups which can be employed in this new molecular tailoring procedure. Other examples of surface moieties which also provide the reactivity required for this purpose include optional leaving or coupling groups such as, for example, other halogens (Cl and I), carboxylic (—COOH), acid halide (—COX, where X represents a halogen), anhydrides [C(O)OC(O)] groups, thiol (SH) groups, aldehydes (—CHO), ketones (CH$_2$=O), and the like. Using either the low duty cycle pulsed or low power CW plasma deposition technique and appropriate monomer, the present invention has succeeded in deposition of these groups on solid surfaces. These groups were then readily reacted with various nucleophiles, again using a simple one-step coupling process carried out at ambient temperatures.

An important component of the present invention involves the successful retention of the reactive groups of the monomers during the plasma induced film formation processes. In general these functional groups (e.g. —COCl, —COOH, —CHO) represent chemical structures which are all too readily destroyed during energetic plasma polymerization processes. In many cases, this destruction reflects the favorable energetics involved in formation of products such as CO or CO$_2$ which thus represent loss of the key functionality of the monomers. However, as documented in the present invention, it is clearly possible to retain these reactive groups in the plasma modified films if unusually low powers are employed during the plasma deposition steps. However, as anyone who is well versed in the practice of plasma polymerizations will recognize, the correlation between applied electromagnetic power and the plasma generated film composition is complicated by the fact that many other process variables must also be simultaneously considered. These additional variables include such factors as the size (e.g., volume) of the reactor chamber, the location of the substrates relative to the plasma discharge zone, the monomer flow rates, the monomer pressure, the nature of the monomer, etc. For example, it is well known that increased monomer functional group retention can be maintained at a given power by increasing the monomer flow rate (Yasuda). Likewise, the use of a large reaction volume at a given applied power would also provide increased retention of monomer functional groups, as this variation in effect decreases the power density during the plasma polymerization process. Similarly there are many studies which have shown that location of substrates downstream of the electrodes employed to power the discharge will provide surface coatings having increased incorporation of monomer functional groups. This observation reflects the fact that as the substrate is moved progressively away from the discharge zone there is a pronounced decrease in the intensity of the electromagnetic field and thus development of less harsh reaction conditions. In other words, although a relatively high power may be employed to power the discharge between the electrodes, the effective power governing the chemistry either up-stream or down-stream of these electrodes would, in fact, be extremely low. Nevertheless significant film formation has been observed at these plasma remote positions.

In particular, quantitation of the power requirement is severely complicated by the strong dependence of functional group retention on the nature of the monomer (and functional group) and the power employed. This dependency is clearly illustrated in the present invention in comparing the power dependence of Br atom retention in the allyl bromide plasma polymerization to that observed in the retention of the —COCl group during polymerization of acryloyl chloride. With respect to this comparison, we introduce the concept of average power, which for pulsed plasma depositions is defined as:

$$\langle \text{Avg. Power} \rangle = \frac{\text{plasma on time}}{\text{plasma (on + off) time}} \times \text{peak } RF \text{ power}$$

Figure 9:
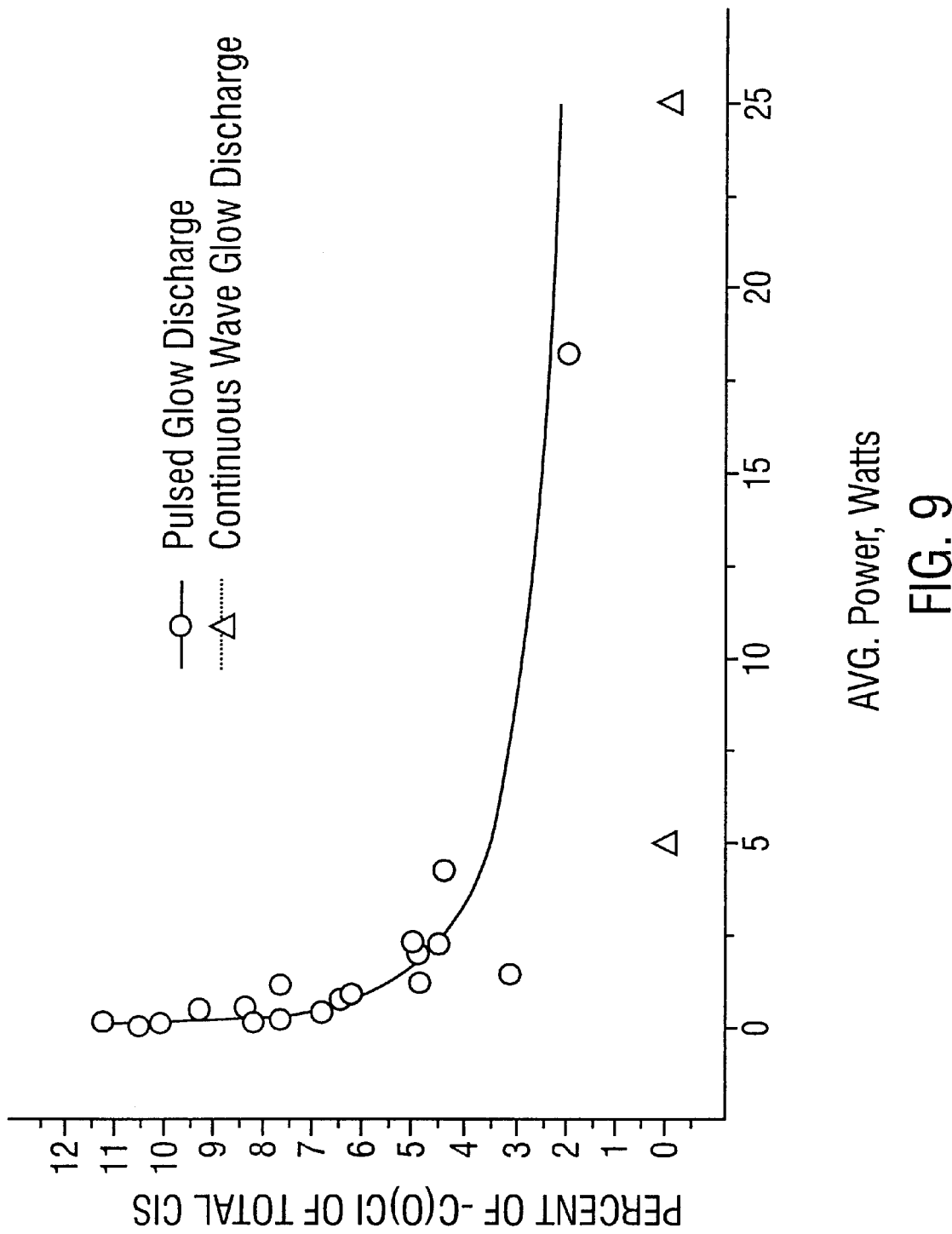
FIG. 9 shows relative amounts of acid chloride functionality retained in the surface film as a function of average radiofrequency power.

As shown in FIG. 1, it is possible to retain large portions of the C—Br functionality of the allyl bromide monomer in a pulsed plasma run of 3 ms on and 15 ms off at a peak power of 200 watts. (FIG. 1C). This corresponds to an average power, as defined above, of 33 watts. Under this condition, the plasma generated film contains one bromine atom for every 3.94 carbon atoms. This can be contrasted with one bromine for each 3 carbons in the starting monomer, thus representing a significant retention of Br atoms in the plasma deposited film. In contrast, the experiments with acryloyl chloride, in the same reactor and at essentially the same monomer flow rate and pressure as employed with allyl bromide, results in essentially zero —COCl functional group retention if plasma polymerization were carried out at an average- power of 33 watts. (FIG. 9). In fact, it is only at average powers of less than approximately 5 watts that significant —COCl retention is observed during plasma polymerization of this monomer under the particular combination of experimental conditions employed, as shown in FIG. 9. Wide ranging variations in the minimum power requirements needed to retain functional group incorporation in the plasma generated films have been observed in comparing other monomers under similar deposition conditions. For example, it requires significantly lower average power to retain C—I bonds in the plasma polymerization of allyl iodide versus that observed with allyl bromide.

In light of the above considerations, it is simply not possible to define a specific wattage value to be defined as "low wattage" for the purpose of this invention. The fact of the matter is that the specific low wattage value required to retain a specified percentage of monomer functional groups will vary with each monomer and with variations of the other processing variables, as noted above. Therefore, as those schooled in the art will recognize, the important feature is to adjust the plasma deposition conditions to the point at which the desired incorporation of reactive functional groups in the plasma deposited film is achieved. This desired incorporation can be achieved in many different ways, all of which have, for the sake of simplicity, been categorized under the "low power" concept. Thus, changing process variables such as the reactor volume, location of substrates, flow rate of the monomers [i.e. the W/F parameter (Yasuda)] are all understood to be able to provide lower power deposition conditions as used in the context of the present invention.

In light of the above discussion, coupled with the documentation of retention of the highly thermodynamically unstable —COCl and —COOH groups in this invention, it is clear that the low power plasma polymerization process, particularly the pulsed plasmas, can be utilized to provide surface films having an enormous range of reactive functional groups. For example, in addition to the specific monomers identified above and in the Examples, it is clear to those skilled in the art that the initial surface functionalization plasma step could be employed with virtually any volatile monomer having a desired functional group. The present invention clearly illustrates this fact with several monomers having reactive groups which are normally loss under typical plasma polymerization conditions (e.g. —COCl and —COOH). Nevertheless, it is shown herein that these reactive groups are retained as intact entities under the exceptionally mild plasma deposition conditions employed in this invention. Obviously this technology can be extended to include a rich and diverse range of additional functional groups. For example, the following list of allyl type compounds represents a partial listing of additional functional groups which could be deposited as intact entities for further chemical derivatizations:

| MONOMER | FUNCTIONAL GROUP |
|---|---|
| allyl isothiocyanate | —NCS |
| allyl cyanide | —CN |
| allyl benzene | —$C_6H_5$ |
| allyl acetate | —COOR |
| allyl mercaptan | —SH |
| allyl glycidyl ether |  |
| allyl ether | C—O—C |
| allyl chloroformate | —COOCl |
| allyl methyl sulfide | C—S—C |
| allyl phenyl sulfone | —$SO_2$C |
| allylphosphonic dichloride | —$CP(O)Cl_2$ |
| allyltrimethylsilane | —$Si(R)_3$ |
| allyltriethoxysilane | —$Si(OR)_3$ |

The above partial listing has focused on allyl type compounds since these materials have favorable vapor pressures and our experience with other allyl compounds, as described in this invention, documents the fact that retention of these functional groups is clearly anticipated under low power plasma polymerization. Obviously this technology can also be extended to non-allyl precursors, including even saturated compounds as shown in one of the Examples.

With respect to the present invention, the second step coupling reaction of molecules to the plasma treated surfaces, when conducted in a solution, imposes an obvious requirement on the nature of the plasma-introduced reactive functional groups. This requirement centers on recognition that solvolsis of these plasma introduced functional groups must be significantly slower than the competing reaction by solution nucleophiles with these same groups if this invention is to be useful in molecular surface tailoring processes. For example, in the case of aqueous solution reactions, hydrolysis of these plasma deposited functional groups must be significantly slower than the competing nucleophilic displacement reactions. The present results clearly show that this requirement is satisfied for selective surface functional groups, such as the C—Br group illustrated previously.

There are many applications for the technology described in this invention. Certainly one important applications area will be in the biomaterials field, specifically providing surface modifications to improve biocompatibility of these materials. In some of these applications surface modifications are required to improve the adherence of biomolecules (e.g., proteins, glycosaminoglycan, cellular materials, etc.) to surfaces, particularly those surfaces involved with blood contact. The present proposal offers an unusually facile approach to structuring surfaces which will promote these biomolecular adsorption processes. Recent work has shown that attachment of specific peptide sequences (e.g., YIGSR and RGD) to surfaces is particularly effective in promoting adsorption and growth of specific cells. The process described in the present invention provides a simple approach to surface attachment of these peptides and any other peptide, where this attachment is accomplished from aqueous solution. The aqueous solution capability is particularly significant in that this solvent permits retention of the geometrical structures of these peptide molecules. These geometric considerations can be very important with respect to promoting biomolecule adsorptions. Alternately, it is clearly possible to covalently attach biomolecules (such as saccharides, proteins, etc.) directly to the plasma functionalized surfaces via simple covalent bond formation. For example, the amino and sulfhydryl groups of molecules such as enzymes will couple directly to surface containing reactive groups such as C—Br, C—COCl, etc. Similarly, biologically important molecules such as heparin will also bind to these surfaces via their amino groups.

Clearly, the technology described in this invention can be employed with molecules other than peptides, glycosaminoglycans and the like to promote improved biocompatibility of materials. For example, many biomaterial applications require biologically non-fouling surfaces (i.e., surfaces which minimize or eliminate cellular or biomolecule adsorptions). Research from many laboratories has shown that surface-attached polyethylene glycol (PEG) molecules are particularly effective in reducing biomolecule adsorptions. The surface modification procedure described herein is ideal for this purpose in that PEG molecules can conveniently be bonded to the plasma modified surfaces. This may be an aqueous bonding process, taking advantage of the water-solubility of PEG molecules. In a preferred embodiment, the PEG molecules employed are terminated with —$NH_2$ groups which can conveniently be coupled to the plasma deposited functional carbon-bromine groups as shown herein. With other attached functional groups, e.g. acyl halide, PEG can be directly attached.

The biomaterials example represent but one of many applications for this new surface modification procedure. As those schooled in the art will recognize, this process can be applied advantageously to any device in which surface chemistry exerts an important role in the device function. For example, this process can be employed to molecularly tailor surfaces for improving the performance of devices such as sensors, heterogeneous catalysts, permselective membranes, etc. It could also be employed for improved coating applications such as those involved in anti-corrosion and passivation coatings, optical and dielectric coatings, etc. Each such application simply involves the surface attachment of selected molecule(s) required to improve the performance of a particular device, using the simple two-step approach described herein.

An additional feature of the present invention is the molecular tailoring of surfaces where selective attachment of more than one kind of molecule is achieved. In this process, the initial plasma deposition is employed to simultaneously deposit two or more functional groups via use of appropriate monomer mixtures. Subsequently, selective chemical attachment reactions are employed to attach different molecules to each functional group introduced by the plasma deposition process.

The surface modification procedures described herein can be illustrated by reference to specific functional groups as involved in selective surface attachment of two different kinds of molecules. For example, the plasma process is employed to simultaneously introduce C—Br and —COCl surface groups via use of an appropriate monomer mixture such as allyl bromide and acryloyl chloride. The —COCl acid chloride groups are significantly more reactive than the C—Br groups. For example, under most conditions the acid chlorides, but not the carbon-bromides, react with alcohol molecules:

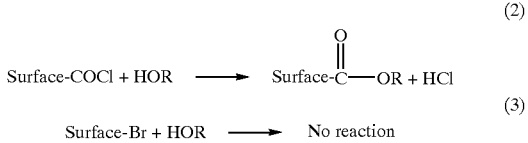

(2)

(3)

Thus selective attachment of the alcohol molecule can be carried out at the acid chloride sites. Subsequently, solution molecules can be attached to the C—Br sites, using stronger nucleophilic reagents such as —$NH_2$ groups, as previously described in reaction (1). In this way, the molecular tailoring process can be conveniently employed to covalently bind two different types of molecules to a particular surface. Further, the relative concentrations of the covalently bonded molecules to the surface is easily controlled by simply varying the relative partial pressures of the two monomers employed during the plasma deposition process. It should also be noted explicitly that the R groups denoted in the above coupling reactions may also contain specific functional groups which could be utilized in subsequent further coupling reactions to the solid surfaces. As one of many such examples, the R group may contain an unsaturated bond which could be utilized for additional molecular tailoring reactions. Such a process is illustrated in reaction 4.

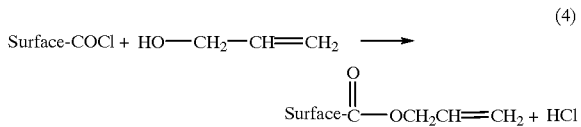

(4)

Clearly, the alkene appendage now affixed to the surface provides an additional route to further important coupling reactions including particularly synthesis of catalytic materials. As those schooled in this art will readily recognize, the nature of the R groups introduced in reactions such as (2) and (4) (i.e., during the initial coupling process) will provide a rich and diverse range of additional surface coupled reactive groups to be employed in molecular construction of surfaces for diverse applications.

Although the above descriptions have focused on the use of solution reactions in the reactive coupling of targeted materials to the plasma modified surfaces, as those schooled in the art will readily recognize this second step coupling reaction could equally well be carried out by vapor phase reactions. For example, the reaction shown above (reaction 4) could equally well be carried out using allyl alcohol vapor. Alternately, the coupling process could initially utilize an initial plasma deposition of allyl alcohol to provide surface hydroxyls which are thus reacted with acryloyl chloride vapor, as shown below:

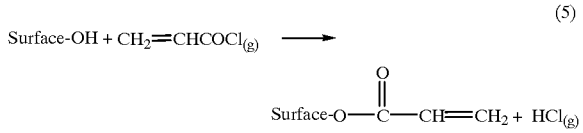

(5)

In this latter reaction, use is made of the high volatility of acryloyl chloride relative to allyl alcohol. Obviously, the vapor phase coupling reactions could include a rich and diverse range of reactants including variations in the surface attached groups and the reactive functional groups of the vapor phase materials. As in the solution coupling reactions, the temperatures of the system would be adjusted to provide reaction rates of desirable proportions.

Based on the above description, it is clear that this procedure can be employed to introduce a multitude of surface functionalities having varying degrees of reactivity. By carrying out sequential derivatization reactions, a molecularly tailored surface having a number of different covalently bonded molecules is readily created. Allyl derivatives are preferred for the plasma depositions of the present invention because of their ready availability, volatility and low costs. They are not however the only possible materials. Any volatile carbonaceous compound having an active functional group may be used.

A major advantage of the use of the plasma process to introduce the reactive surface groups during the initial surface treatment is that this approach permits surface tailoring of virtually any solid substrate. Additionally, the plasma process provides uniform, pin-hole free coatings and they can be applied to any solid without regard to geometric considerations. The present inventors have successfully applied this coating procedure to solids such as polymers, ceramics (including glass), silanized glass, fabrics, paper, metals, silanized metals, semiconductors (e.g., silicon) carbon and even hydrogels.

A problem frequently encountered with plasma deposited coatings is poor adhesion of these films under low energy plasma conditions such as those encountered during low duty cycle pulsed and low energy plasma conditions. While such films may have uses of their own, separate from a substrate, and to that extent are a part of the present invention, adhesion to the substrate is a preferred aspect of the present invention. The present invention involves the discovery that the adhesion of these plasma films to the underlying substrates can be dramatically improved via use of a gradient layered technique. In this process, the plasma deposition is initiated at a high RF duty cycle and a high RF power to provide an underlying initial coating strongly grafted to the solid substrate. The RF duty cycle of the pulsed plasma is then progressively decreased, with this decrease providing increasing retention of the monomer functional groups, as shown in FIG. 1A–1D for an allyl bromide film. In this way, the successive plasma deposited films are tightly bonded to each other, providing a layered structure in which a gradient of monomer functional groups is present. The process is terminated at the lowest RF duty cycle needed to introduce a required surface density of the reactive functional groups. Alternately, the gradient layering technique can be carried out under CW conditions with the RF power being progressively decreased during the plasma deposition process. In this way, a strongly adherent film is deposited with the outermost layer containing a high surface concentration of the desired reactive functional group. This gradient layering technique has been successfully employed to deposit plasma films on a wide range of solid substrates. The term "film" as used herein, those of skill in the art recognize that this may but does not necessarily mean an intact film in the usual sense and may vary in thickness, as a film, from 1 to 3000 Angstroms or may be more widely dispersed non-interacting pendant groups. These films are sufficiently well anchored to the underlying substrates to preclude delamination when subjected to prolonged immersion in various solvents, particularly including pure water and aqueous solutions.

Although the gradient layering technique described above has been found to be useful in improving adhesion of plasma deposited films to various substrates, there are other substrates (e.g. glass, metal and silicon) in which delamination of the gradient layered plasma films is observed after prolonged immersion of the coated substrates in solution. An important aspect of the present invention is the discovery that this delamination problem can be solved via use of a plasma deposited sub-layer which helps to bridge the inherent incompatibility encountered between an inorganic substrate (such as glass, metal or silicon) and the gradient layered organic plasma deposited coating. An example of this sub-layer technique is silanizing, the use of a plasma deposited film from hexamethyldisiloxane (HMDSO) to successfully anchor a plasma-generated organic film (e.g. a film from allyl amine or allyl bromide) to an inorganic substrate (e.g. silicon or glass). In these experiments, the organic plasma film was deposited using the gradient layering technique described earlier.

The insertion of the HMDSO intermediate sub-layer between the glass, silicon or metal surface and the carbonaceous outer layer functionalized plasma films works remarkably well in strongly anchoring these outer organic films to the non-organic substrates. For example, films which previously delaminated from these non-organic substrates a few minutes after sample immersion in aqueous solution, have been observed to remain strongly bound to the substrates, without noticeable changes in chemical composition, after many weeks of immersion when the HMDSO sub-layer is present.

As those schooled in the art will recognize, the effectiveness of the intermediate HMDSO sub-layer in improving the adhesion of the organic films to the chemically different solid substrates is an example of but one of many sub-layers which might be employed to achieve this goal. In particular other organo-silicon compounds, such as silanes and other siloxanes are expected to be particularly effective in this application (either being used to "silanize" a solid surface of the present invention). Other monomers which are capable of bridging the chemical dissimilarities between organic and inorganic materials should also provide this important function. Examples of such monomers would include volatile organo-metallic compounds such as tetramethyl tin, furocene, tetramethyl lead, etc. which are known to provide organo-metallic films under plasma polymerization conditions.

A further aspect of the present invention is to employ the low duty pulsed or low power CW plasma process to deposit fluorocarbon films of exceptionally high hydrophobicity on solid substrates. These ultra low energy surface coatings can be employed directly for specific applications or they could be coupled with simultaneous deposition of a reactive functional group by combining the fluorocarbon monomer with an appropriate functionalized monomer. In the latter case the plasma generated surface consists of highly hydrophobic regions, except for those locations occupied by the reactive functional groups. These reactive groups are available for subsequent chemical derivatization reactions as described previously.

An aspect of the present invention is the discovery that the use of a highly —$CF_3$ substituted fluorocarbon monomer can yield exceptionally hydrophobic surfaces via plasma deposition. For example, utilizing low duty cycle RF plasma deposition it is possible to retain, to a very high degree, the —$CF_3$ content of the starting monomer. An example of this —$CF_3$ retention is shown in FIG. 2 which provides high resolution C(1s) ESCA spectra of fluorocarbon films obtained from an isomeric mixture of substituted perfluorohexenes. As shown in FIG. 2, there is a clear-cut increased retention of the —$CF_3$ groups of the starting monomer as the RF duty cycle employed during the deposition was decreased. Alternately, the same general increased —$CF_3$ retention can be achieved under CW plasma deposition conditions by reducing the RF power. These effects are clearly shown in FIG. 3.

Figure 2A:
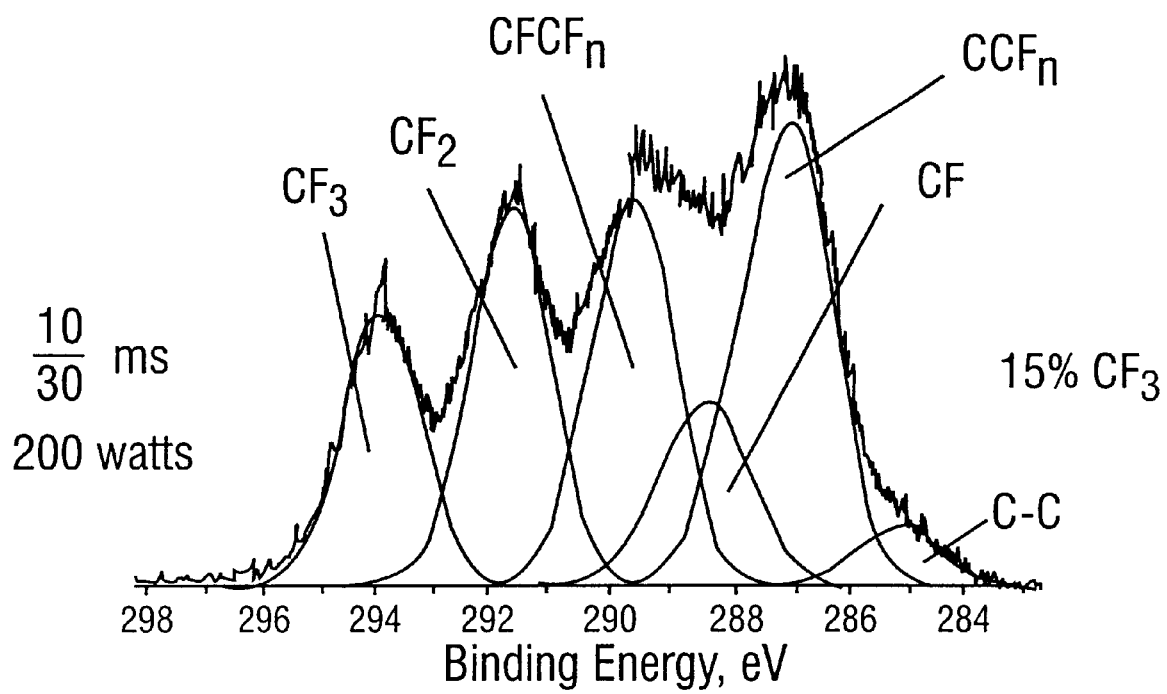
FIGS. 2A–2C. High resolution C(1s) XPS spectra of pulsed plasma polymerized films of the $C_9F_{18}$ monomers. RF duty cycles and peak power employed are shown for each film.
Figure 2B:
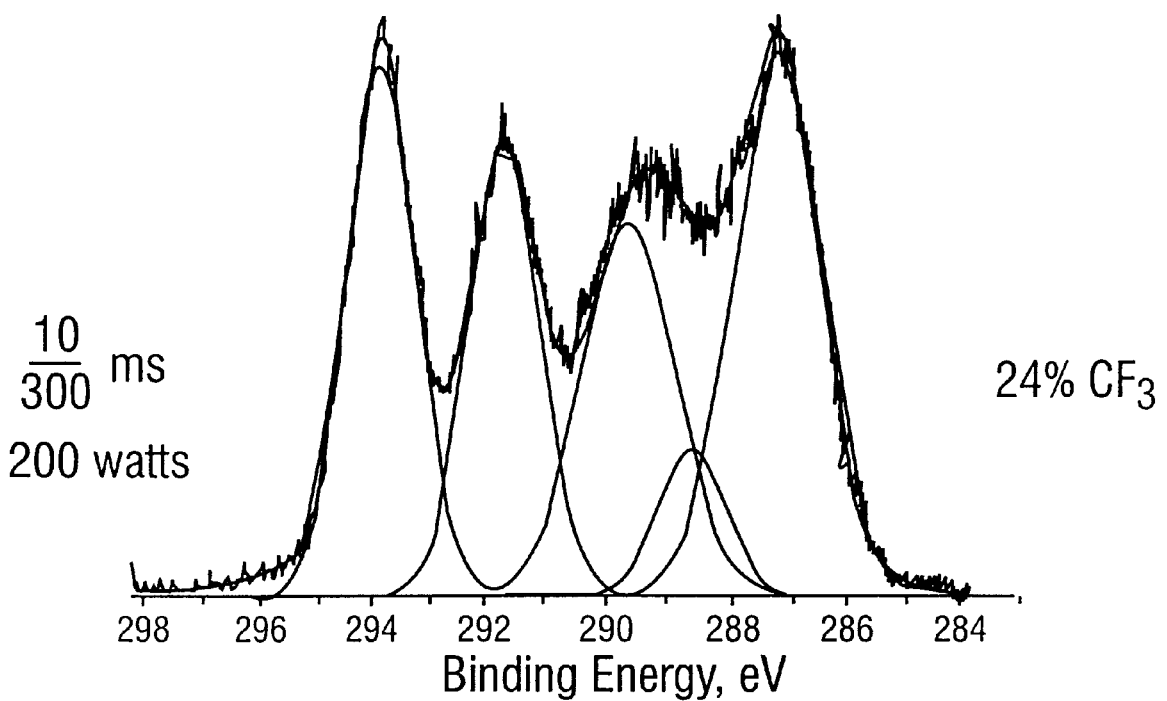
Figure 2C:
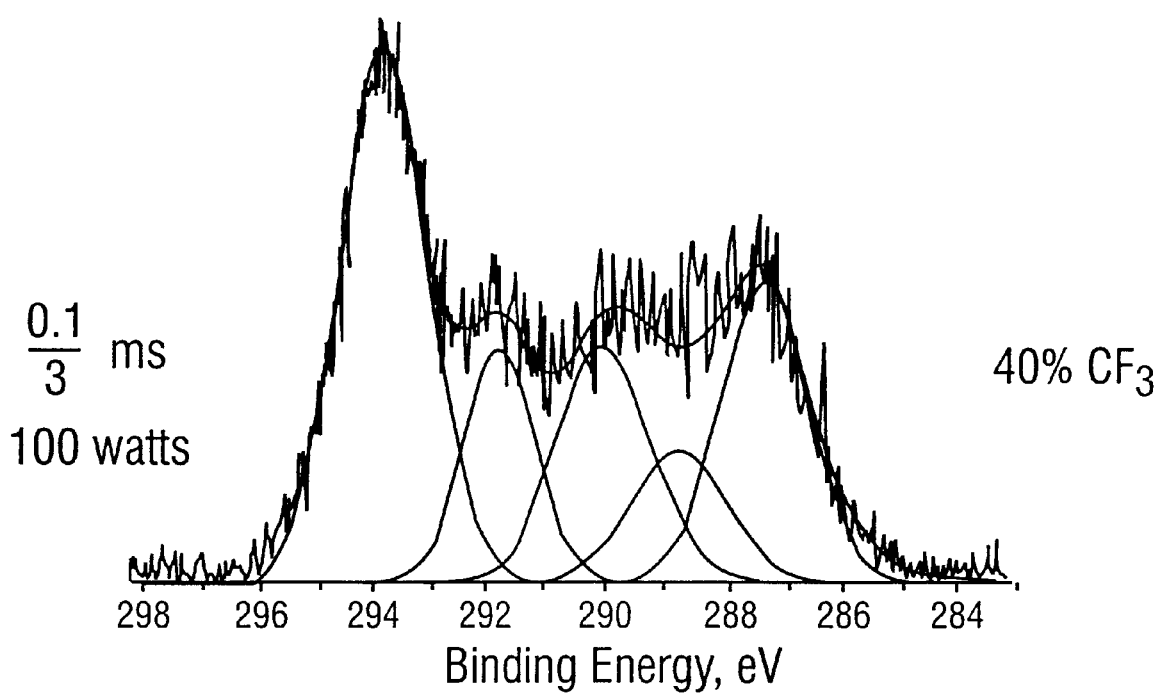
Figure 3A:
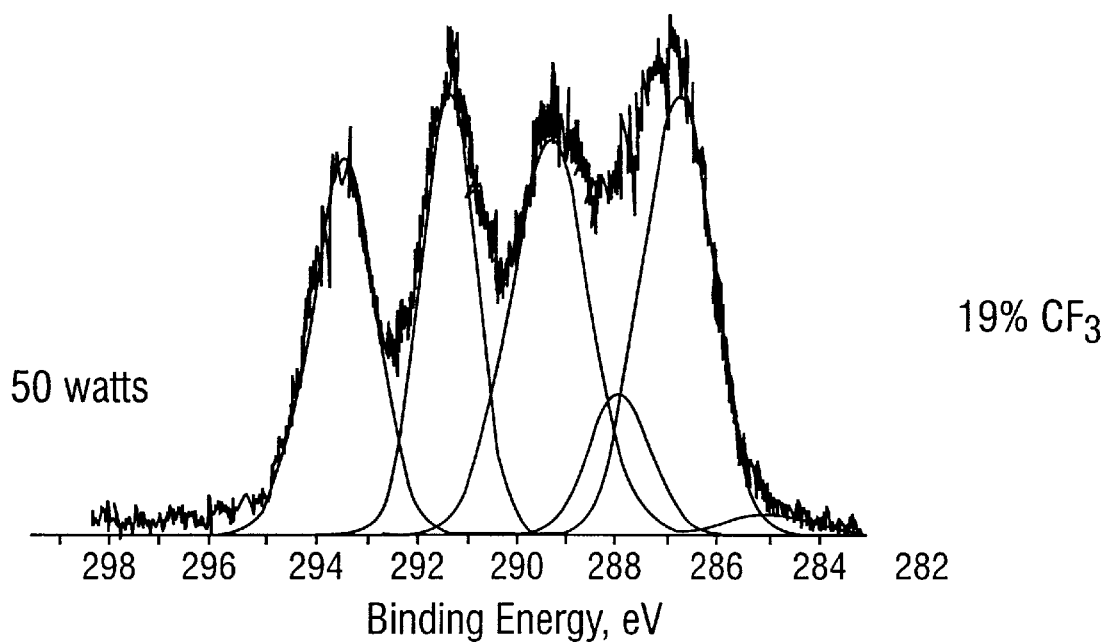
FIGS. 3A–3B. High resolution C(1s) XPS of polymerized $C_9F_{18}$ films obtained under CW plasma conditions of 50 and 5 watts, as shown.
Figure 3B:
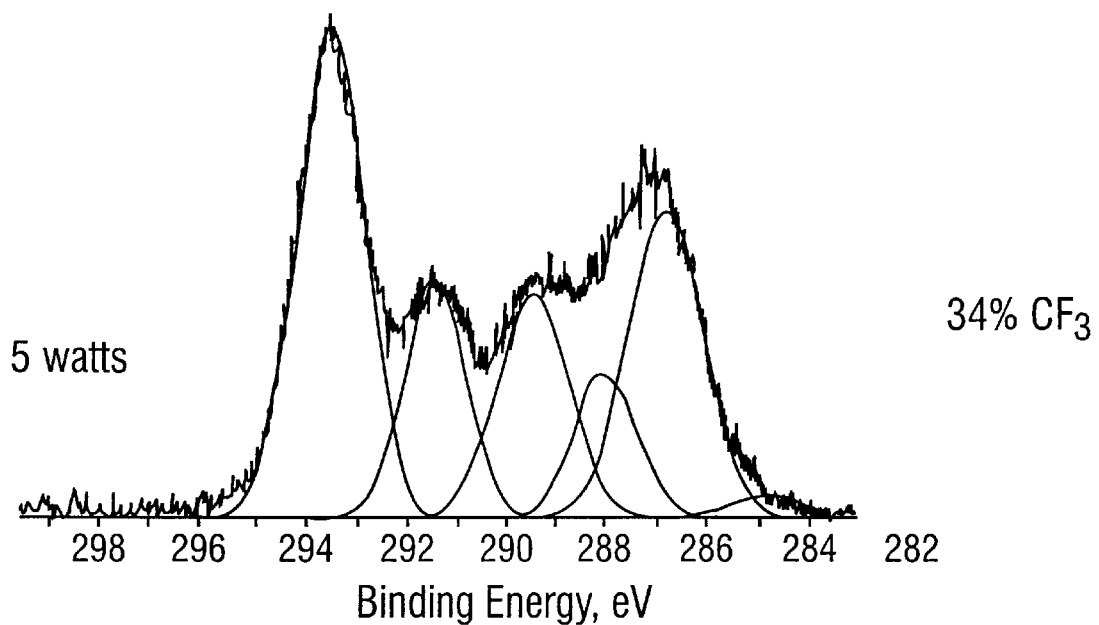

FIG. 2B shows the ratio of the relative peak areas of $CF_3$ to $CF_2$ as being approximately 1.19, and FIG. 2C shows the ratio of relative peak areas of $CF_3/CF_2$ as being about 3.15; while FIG. 3B shows a ratio of relative peak areas of $CF_3/CF_2$ of about 2.17. Thus, the $CF_3/CF_2$ carbon ratio ranges from about 1.2 to about 3.2.

Using the plasma deposition approach and the highly —$CF_3$ substituted monomer it is possible to generate a film whose hydrophobicity exceeds that of conventional Teflon® surfaces. (see FIG. 4.) Both the advancing and receding water contact angles are higher than those observed with a conventional Teflon® (i.e., —$CF_2$ dominated) fluorocarbon film. (see FIG. 5).

Although the above discussion has been illustrated with perfluorohexene monomers, those skilled in the art will readily recognize that other highly —$CF_3$ substituted monomers (such as, e.g., other volatile perfluorinated compounds, particularly perfluorocarbons) can be employed under low energy plasma conditions to provide —$CF_3$ dominated films. Either the low duty cycle pulsed plasma or the low power CW plasma would be useful in providing retention of the original —$CF_3$ monomer content in the plasma generated films.

By incorporating an appropriate functionalized monomer in with a highly —$CF_3$ substituted monomer, the plasma deposition process may be used to produce a surface coating which is hydrophobic but at the same time, susceptible to covalent attachment of other molecules at the reactive functional group site. The extent of surface coverage by this functional group is easily adjusted by variation of the relative concentration of the added functionalized monomer in the gas mixture employed.

In one particular embodiment of this invention a functionalized fluorocarbon surface capable of ready attachment of other molecules is prepared using a functionalized fluorinated monomer which is added to the heavily —$CF_3$ substituted primary monomer. In this way the entire surface coating consists of carbon and fluorine atoms with the exception of the sites occupied by the reactive functional groups. An illustration of this invention is plasma deposition of a mixture of bromotrifluoroethylene and the substituted perfluorohexene mixture noted previously. The resulting film is extremely hydrophobic, highly nonadsorbent for biological molecules and chemically inert except for the sites occupied by C—Br bonds. The C—Br can then be used to bind other molecules to the surface, using a simple one-step coupling reaction.

Surfaces modifiable by these processes include (but are not limited to) polymers, glass, ceramics, carbon, fabrics, paper, metal, semiconductors, wood, composites, cellulose, films (particularly polymeric films) and hydrogels.

EXAMPLE 1

Figure 6:
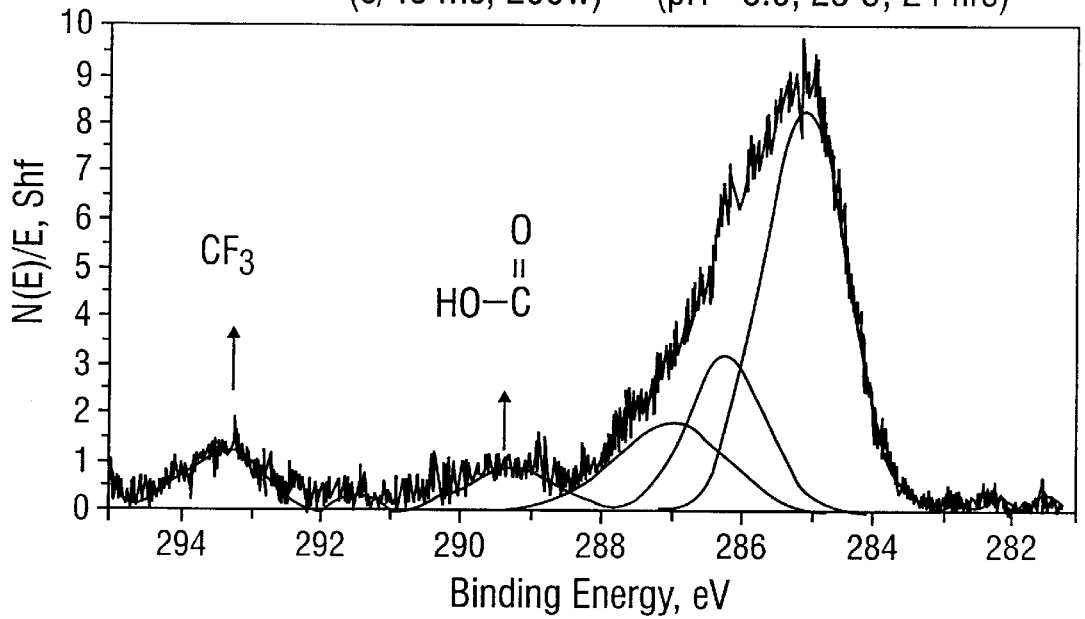
FIG. 6 shows a high resolution ESCA spectrum of an allyl bromide surface coupled with hexafluoro-DL-valine.

A variable duty cycle pulsed RF plasma was employed using allyl bromide monomer to deposit a thin film containing C—Br bonds on the surface of a polymer (Dacron®) substrate. This film was deposited using an RF peak power of 200 watts and an initial RF plasma duty cycle of 3 ms on and 5 ms off. The monomer pressure was~35 m Torr and the flow velocity was 3.5 cm³/cmin (STP). After 3 minutes of plasma operation, the RF duty cycle was reduced to ⅗s, then ¾s and finally ¾₆₀ (plasma on to plasma off times, in ms). This procedure provided a gradient layered film with good adhesion to the underlying Dacron® [polyethyleneterephthalate, (PET)] substrate and with a relatively high density of surface C—Br groups. (Surface Br atom content was 26% relative to 74% carbon atoms). Subsequently this surface modified sample was immersed in an aqueous solution which contained the amino acid hexafluoro-DL-valine at a concentration of 20 mM. After 10 hours reaction at room temperature and a pH of 8.0, the coated Dacron® sample was removed, rinsed many times (including washing with a surfactant solution containing dissolved 1% sodium dodecyl sulfate (SDS), vacuum dried and then subjected to ESCA analysis. The ESCA analysis revealed clearly the presence of the trifluoromethyl groups of the fluorovaline along with the presence of surface nitrogen from the amine group and oxygen from the carboxylic acid group. The high resolution C(1s) ESCA spectrum of this sample is shown in FIG. 6. These results reveal that the molecular tailoring of the surface, in this case the addition of the amino acid hexafluorovaline, was successfully achieved via the simple two-step process involving plasma deposition followed by the room temperature derivatization reaction.

EXAMPLE 1A

A pulsed plasma process was employed to deposit a bromine-containing organic film on a PET substrate. However, in this work dibromomethane, $CH_2Br_2$, was employed as monomer gas in lieu of the allyl bromide monomer used in Example 1. Again a gradient layering technique was employed to provide good adhesion between the plasma deposited films and the underlying solid substrate. The overmost layer of the plasma generated film contained 19 atom % Br relative to carbon atom content, as shown by ESCA analysis. This sample was then immersed in a 20 mM cysteine aqueous solution at pH 8.0 and room temperature for 24 hours. Subsequently the sample was removed from solution, subjected to thorough rinsing with SDS solution and distilled water, and then vacuum dried. The sample was then subjected to ESCA analysis which revealed the presence of S, N and O atoms on the surface indicating the presence of covalently bound cysteine molecules. However the relatively concentration of surface bound cysteine molecules was notably less than that achieved with allyl bromide films. This example clearly indicates that the monomer precursor employed for the plasma surface modification does not have to be of the alkenic unsaturated type in order to provide reactive surface functional groups which can bind covalently to solute molecules. In this case, the molecular tailoring procedure was achieved employing an alkyl bromide during the plasma modification step.

EXAMPLE 2

The same plasma treatment described in Example 1 was applied to a polished silicon substrate, in lieu of the Dacron® sample employed in Example 1. However, before deposition of the gradient layered bromine containing film, a thin sublayer film of hexamethyldisiloxane (HMDSO) was plasma deposited on the Si sample (silanization). This sample was then derivatized as in Example 1, using the hexafluoro-DL-valine reagent. The same results as shown in FIG. 6, within experimental error, were obtained, indicating that the molecular tailoring achieved by this invention is independent of the nature of the solid substrate. Furthermore, the entire assembly was stable towards immersion in aqueous solution with no evidence of film delamination after prolonged testing.

EXAMPLE 3

A gradient layered plasma generated film was again deposited on a Dacron® (PET) substrate using allyl bromide monomer, as described in Example 1. This C—Br containing surface was subsequently immersed in an aqueous solution containing cysteine. This amino acid was chosen as it contains sulfur as a distinctive label. ESCA analysis of this film after derivatization and thorough rinsing reveals clearly the presence of surface attached sulfur, nitrogen, and oxygen atoms. This result clearly reveals attachment of the cysteine molecules to the surface during the derivatization reaction.

EXAMPLE 3A

A control experiment was carried out in which an untreated PET substrate was immersed in an aqueous solution containing 20 mM cysteine at pH 8.0 and room temperature. After 24 hours immersion this sample was removed, rinsed with SDS solution and distilled water and then vacuum dried. Subsequent ESCA analysis of this film revealed negligible surface content of sulfur or nitrogen atoms. This result shows that successful coupling of the solute molecules to the substrate surfaces requires the presence of reactive functional groups as introduced by the plasma deposition treatment. It also affirms that the solute molecule surface coupling described in the Examples of this invention cannot be simple physical adsorption phenomena as no solute molecule presence is detectable on the unmodified PET substrate.

EXAMPLE 4

Figure 7A:
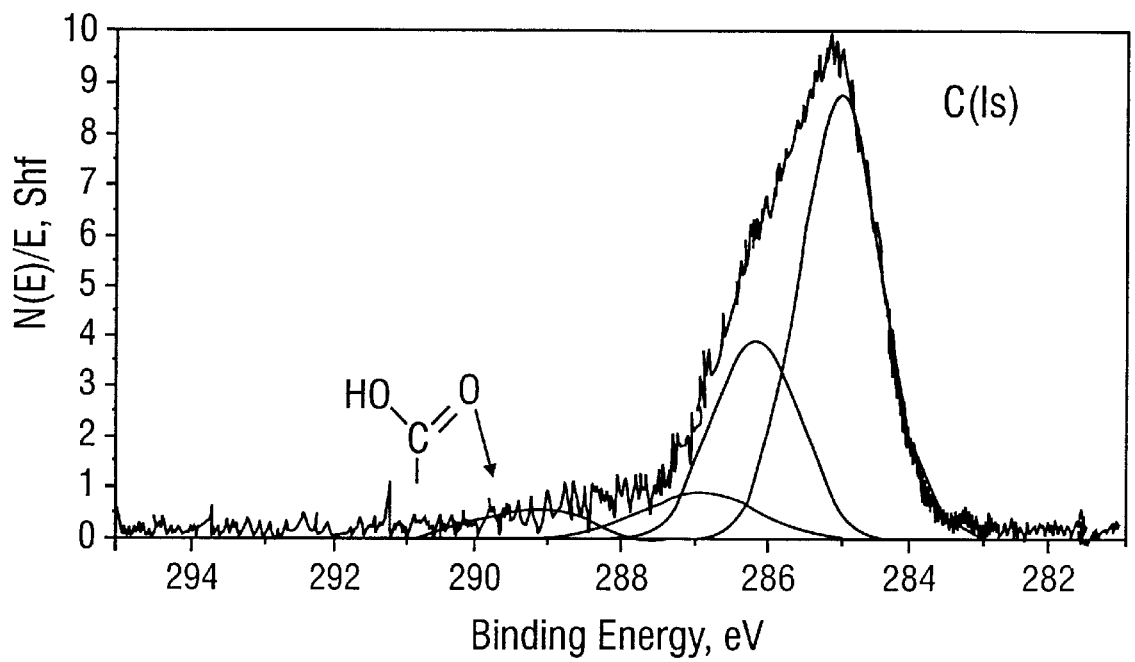
FIG. 7A and FIG. 7B which show a high resolution ESCA spectrum of an allyl bromide surface coupled with YIGSR.
Figure 7B:
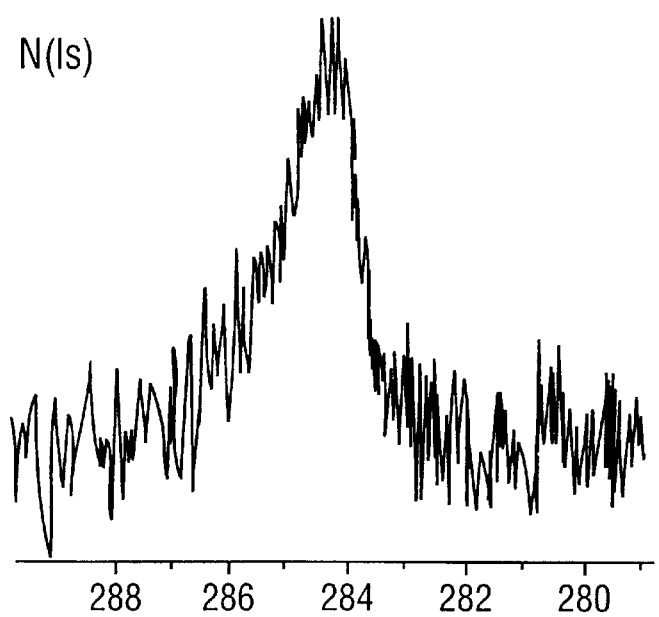

A sample prepared as in Example 1 was subjected to reaction with a solution containing the peptide YIGSR in place of hexafluoro-DL-valine. Subsequent ESCA analysis of this derivatized surface revealed clearly the presence of amine and carboxylic acid groups consistent with the attachment of the YIGSR peptide. The ESCA spectra obtained after attachment of YIGSR molecules is shown in FIG. 7A and FIG. 7B which show the presence of —COOH groups at the high binding energy peak in the C(1s) spectrum [i.e., at 289eV] and the N(1s) ESCA peak (inset).

EXAMPLE 4A

In a separate experiment, the peptide RGD was also shown to bind covalently to a PET substrate initially modified with a plasma deposited allyl bromide film as described in Example 1. Again ESCA analysis of the surface after 10 hour aqueous solution reaction of RGD with the C—Br surface groups was employed to rove the surface attachment of RGD molecules as shown by surface N and O atoms.

The results of Examples 4 and 4A clearly illustrate the utility of this surface tailoring procedure to bind any peptide sequence to the surface of the solid substrates.

EXAMPLE 5

Figure 8A:
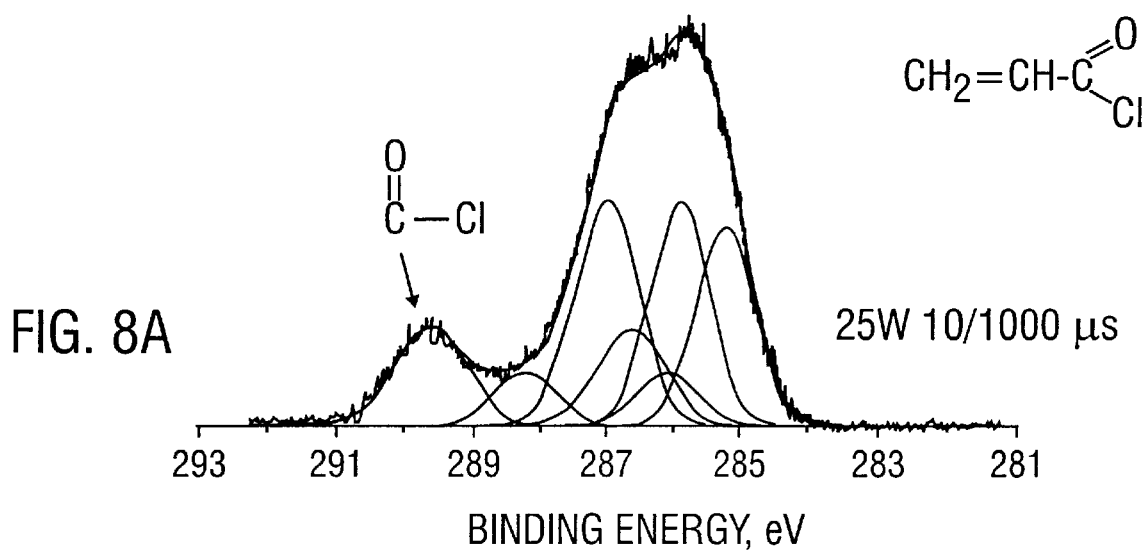
Figure 8B:
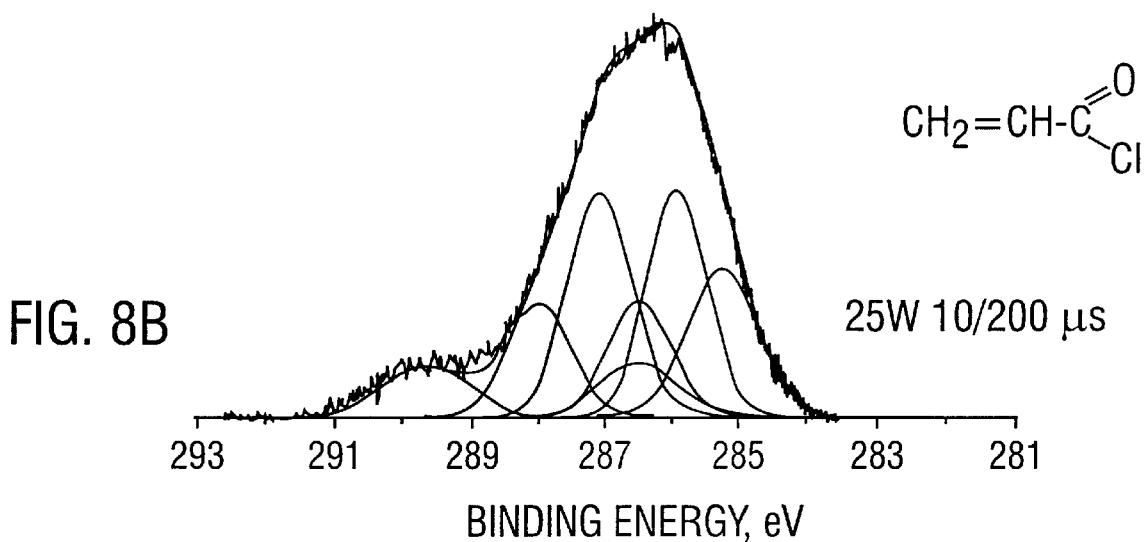

A series of samples were prepared in which acryloyl chloride ($CH_2$=CH—COCl) was plasma deposited onto Si substrates. These depositions were carried out over a wide range of plasma on and plasma off times, as well as under CW conditions. Experimentally it was observed that the composition of the plasma films obtained varied dramatically with the RF duty cycle and/or the RF power density employed during the deposition. In particular, there was a clear-cut and very large scale increase in the degree of retention of the acid chloride group (—COCl) as the RF duty cycle and power were decreased during the deposition. This observation is illustrated in FIGS. 8 and 9. As shown by the high resolution C(1s) spectra in FIG. 8 there is a dramatic increase in the relative surface abundance of the —COCl group (i.e. the peak 289.7 eV) as the RF duty cycle was decreased in this series of runs at 25 watt peak RF power. Also, as shown in this Figure, essentially no —COCl retention was observed in the film deposited at 25 watt CW. FIG. 9 provides vivid evidence for the increased surface incorporation of —COCl groups as the average power during plasma deposition is decreased.

Figure 10:
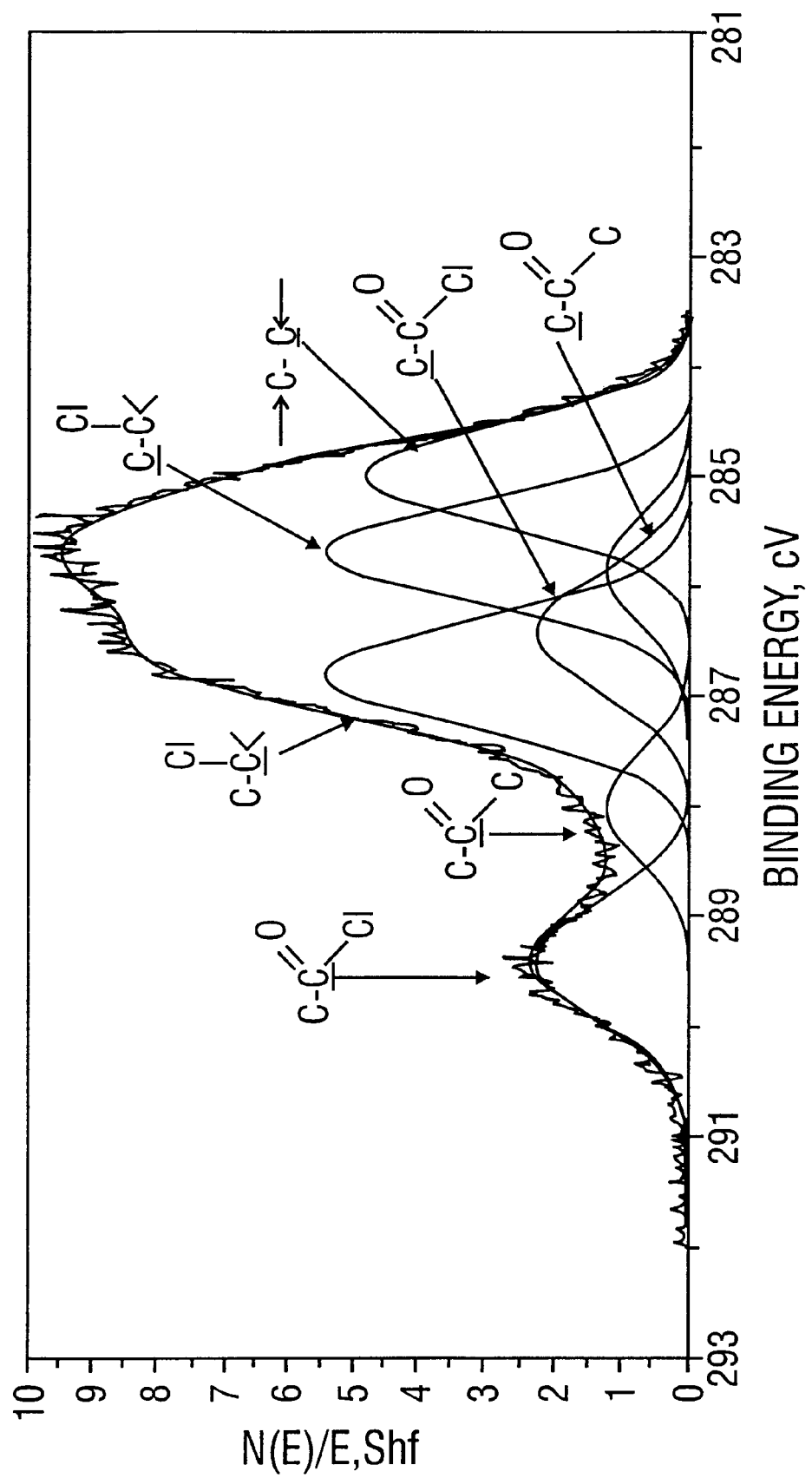
FIG. 10 shows an ESCA curve fit analysis of the C(1s) high resolution spectrum of a film obtained from plasma deposition of acryloyl chloride showing the complete assignment of both chlorine and non-chlorine containing functional groups including the highest binding energy—COCl peak.
Figure 11A:
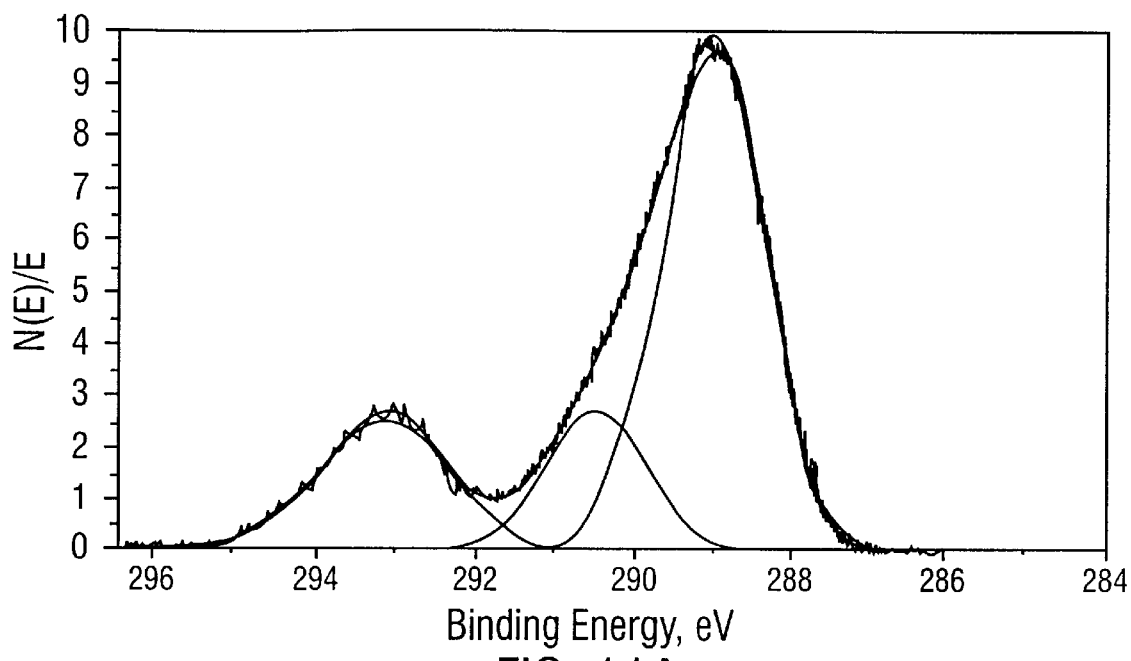
FIGS. 11A–11D show high resolution C(1s) ESCA spectra from acrylic acid films formed at varying plasma deposition duty cycles.
Figure 11B:
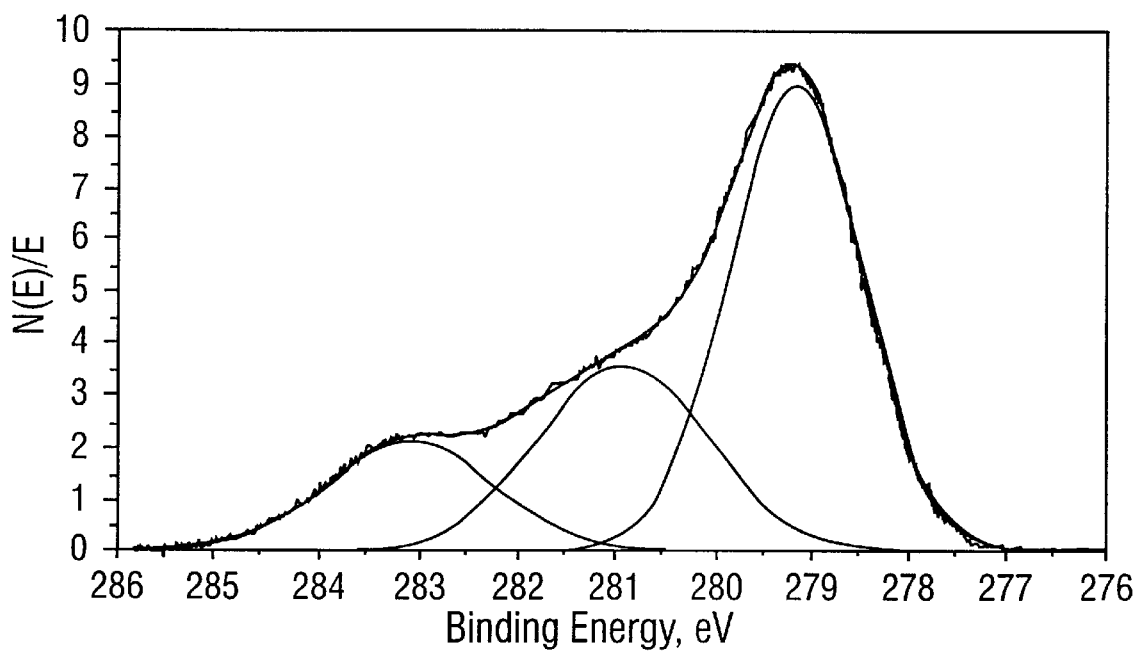
Figure 11C:
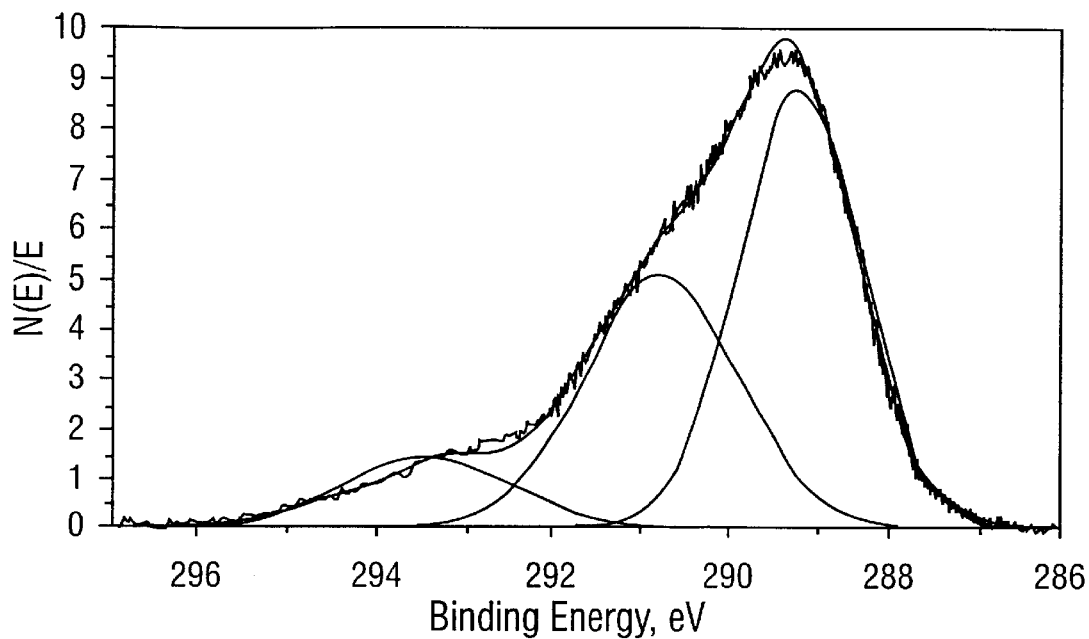
Figure 11D:
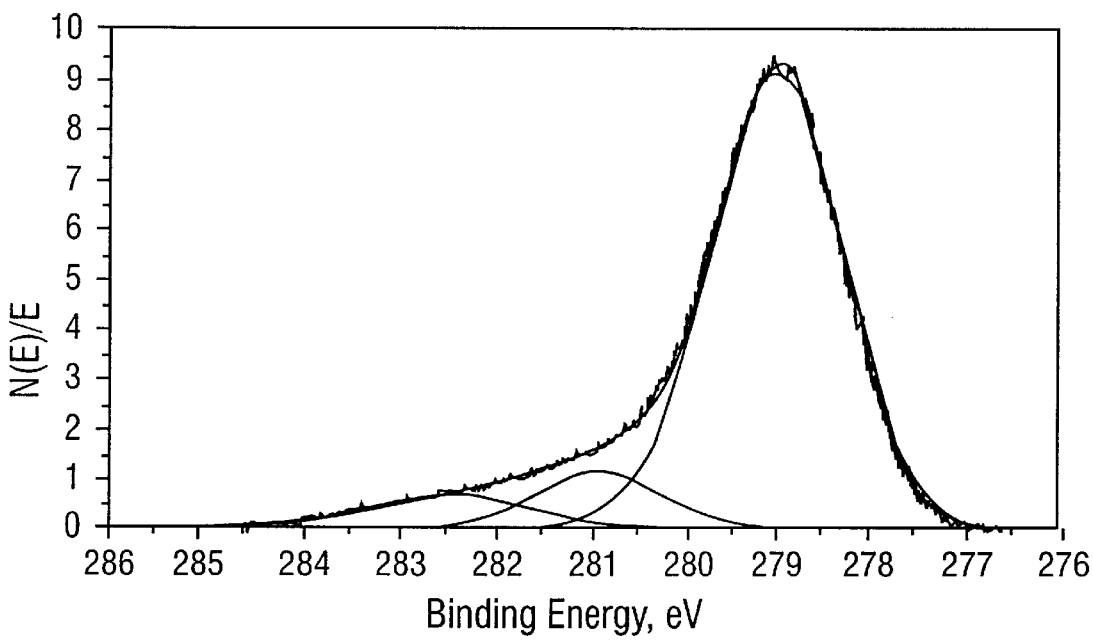

In particular, there is a striking increase in retention of these surface COCl groups as the average power employed drops below 5 watts and, particularly, below 1 watt. For the sake of completeness, FIG. 10 provides a complete functional group assignment of the deconvoluted C(1s) high resolution ESCA spectra obtained from the acryloyl chloride monomer. As the results in FIGS. 8 and 9 clearly evidence, it is possible to both introduce and control the surface density of these reactive —COCl groups using this pulsed plasma and/or low energy CW surface modification technique.

The acid chloride group accounted for some 11% of the total carbon content of the surface layer. Subsequently this film was immersed in a pH 7.4 buffered solution of water. After four hours immersion, ESCA analysis revealed slightly increased oxygen atom incorporation in the film, showing that a small degree of hydrolysis of the surface coating had occurred. This sample was then immersed in an aqueous solution which contained cysteine. ESCA analysis of this film after four hour reaction in this amino acid solution and thorough rinsing clearly revealed the presence of surface attached cysteine molecules as shown by the sulfur and nitrogen ESCA signals. The cysteine surface attachment was slightly higher than that obtained previously with the bromine containing surface.

EXAMPLE 6

A sample was prepared in which a pulsed plasma, 10 $\mu$s on and 1000 $\mu$s off, was employed to deposit an outer film rich in —COCl groups on a PET substrate using the acryloyl chloride monomer. The deposition process involved a gradient layering technique in which an initial high RF duty cycle was gradually decreased to the aforementioned 10/1000 ($\mu$s) value. ESCA analysis of the surface of this sample revealed high —COCl concentration in which this acid chloride group accounted for some 11% of the total surface carbons.

EXAMPLE 7

Figure 12:
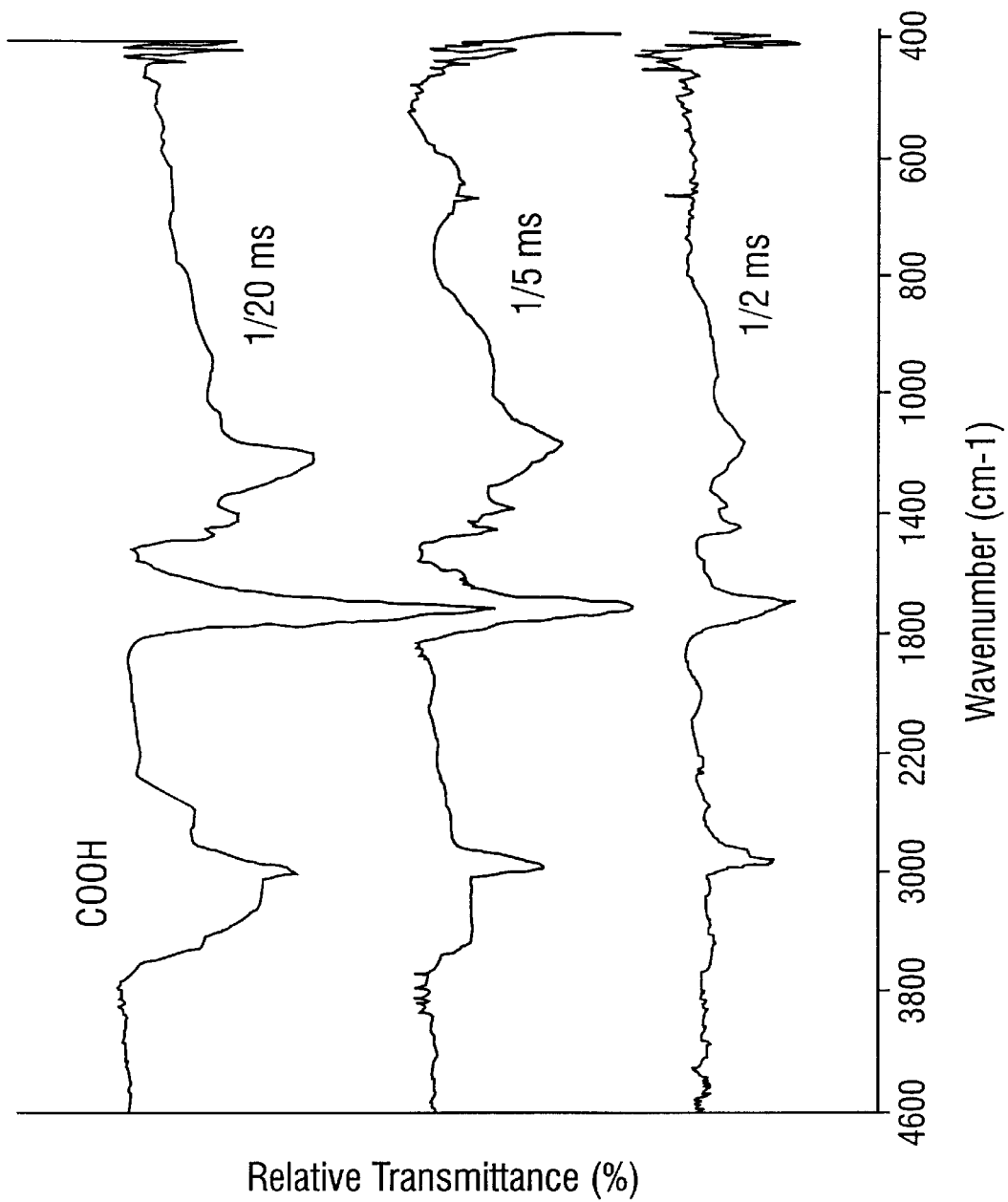
FIG. 12 shows FT-IR absorption spectra of a plasma-deposited acrylic acid films formed at several plasma duty cycles.

Pulsed plasma deposition studies of acrylic acid ($CH_2$=CHCOOH) were carried to provide surface active —COOH functional groups. As noted in previous examples, reduction of the RF duty cycle during deposition leads to increasing incorporation of —COOH groups in the plasma deposition films. This is shown in FIG. 11 in which the high resolution C(1s) ESCA spectra from the acrylic acid plasma film are shown at different RF duty cycles. Clearly, there is a rapid increase in the —COOH content of these films (i.e., the peak at 290 eV) as the RF duty cycle employed during deposition was decreased. Additionally, the increased —COOH content of these films is observed by FT-IR absorption spectra of the plasma generated films as shown in FIG. 12.

Plasma synthesized films of acrylic acid (containing surface active —COOH groups) were subsequently subjected to chemical derivatization reactions. Successful covalent attachment of amines (via formation of amide groups (and alcohols (via formation of ester groups) were demonstrated by surface analysis of these films after the derivatization reactions. These reactions were carried out in both aqueous and non-aqueous solvents.

EXAMPLE 8

A pulsed plasma deposition of allyl bromide was employed to deposit an adherent thin film containing C—Br bonds on a glass substrate. The HMDSO sub-layer and gradient layer of bromide film, as described earlier, were employed to improve the adhesion of this film to the glass substrate. This sample was then immersed in a 20 mM aqueous solution of the amino acid proline for 8 hours at room temperature and a pH of 8.0. Subsequently this sample was rinsed thoroughly with distilled water, 1% SDS solution, more distilled water and then vacuum dried. ESCA and FT-IR analysis of this film revealed the presence of both nitrogen (i.e. amine groups) and carboxylic acid groups now present on the surface of this sample, consistent with the attachment of the proline molecules. This provides a further example of the general utility of this surface modification procedure in that a cyclic molecule (i.e., proline) was successfully attached to the surface. This example also illustrates the utility of the HMDSO plasma deposited sub-layer film to improve the adhesion of subsequent deposited films to the glass substrate. In separate tests, no delamination of the plasma deposited C—Br films were noted after prolonged (i.e. over 3 weeks) immersion of the glass coated samples in aqueous solution at room temperature.

EXAMPLE 8A

A stainless steel (315) substrate was initially coated with an HMDSO sub-layer plasma film followed by the deposition of a gradient layered allyl amine film. This sample was then immersed in aqueous solution. No delamination or film compositional changes were observed after prolonged immersion, as shown by ESCA analysis of the —$NH_2$ surface film before and after aqueous solution immersion.

The combination of examples 8 and 8A are provided o document the efficacy of a HMDSO sub-layer in improving the adhesion of plasma deposited carbonaceous films, including those deposited at low plasma powers, to solid inorganic substrates.

EXAMPLE 9

A pulsed plasma deposition of a trimer mixture of perfluorinated substituted hexenes ($C_9F_{18}$) was employed to a deposit a fluorocarbon film on a silicon substrate. The $CF_3$ content of the plasma deposited film can be controlled via the RF duty cycle employed during the deposition process. This film chemistry controllability is clearly illustrated in FIGS. 2A–2C, which shows increasing $CF_3$ film incorporation as the RF duty cycle employed during the deposition is decreased. For example, a film deposited at a RF duty cycle of 0.1 ms plasma on and 3.0 ms plasma off and 100 watts peak power consists of a composition in which 40% of the surface carbon atoms are present as $CF_3$ groups. This film is exceedingly hydrophobic with a surface energy which is even less than of —$CF_2$— dominated surfaces (such as Teflon®) as shown by water contact angle measurements (see FIGS. 4 and 5). The $CF_3$— dominated film structure, in fact, represents a unique new form of fluorocarbon polymer. The advancing water contact angle was measured to be 127°.

The general reaction system employed in the present work has been described previously (Panchalingam et al., 1993;

1994). The $C_9F_{18}$ was obtained from PCR™, Inc. (Gainesville, Fla.) and consisted of a mixture of three perfluoro-compounds: 2,3,5-trimethylhexene-3; 2,3,5-trimethylhexene-2; and, 2,4,5-trimethylhexene-2. This mixture was subjected to thorough degassing via freeze-thaw cycles but was not subjected to any further purification. All plasma runs were carried out at a $C_9F_{18}$ pressure of 50±2 m Torr and a flow rate of 5.05±0.05 $cm^3$/min (at STP). The plasma generated thin films were deposited on polished silicon substrates and they were subsequently characterized by XPS analysis. These films were also evaluated using the sessile drop water contact angle approach (Rame-Hart type goniometer).

Samples were prepared using both pulsed plasma and continuous-wave (CW) plasma operation. The pulsed plasma depositions involved RF duty cycles (i.e., ratio of plasma on to plasma off times, in ms) of 10/30 and 10/300 at 200 watts peak power and 0.1/3 at 100 watts. The CW runs were carried out at 50 and 5 watts. In terms of equivalent wattages, the pulsed runs approximate the total power of the CW runs when averaged with respect total elapsed times. For example, the pulsed deposition at 10/30 and 200 watts corresponds to an equivalent (or average) power of 50 watts (i.e., 10/40×200).

The XPS film analyses are summarized in Table I and FIGS. 2A–2C (pulsed runs) and FIGS. 3A–3B (CW runs). The C(1s) XPS peak assignment shown are based on the accepted peak identities for fluorocarbon films (Clark and Shuttlerworth, 1980). As shown in Table I, the F/C atom ratio in the films increases with a decrease in average power under both pulsed and CW conditions. The atom ratios shown in Table I were computed from the deconvoluted high resolution C(1s) XPS peaks as opposed to the directly measured F to C values provided by integration of the respective F(1s) and C (1s) peaks. These latter values show the same trends in F to C ratios as reported in Table I. However, they provide values as high as 2.26, which appear to be unreasonably high considering the structures of the C(1 s) peaks. Others have observed comparable results in contrasting the F to C ratios from deconvolution of C(1s) XPS peaks with the values obtained from the separate F(1s) and C(1s) signals (Clark and Shuttlerworth, 1980). As shown in Table I and, as is clearly evident in FIGS. 2A–2C and FIGS. 3A–3B, there is a notable increase in —$CF_3$ incorporation in the film synthesized at a 0.1/3 duty cycle and 100 watts. The $CF_3$ groups represent 40% of the total carbon content of the film. This compares to a theoretical maximum of 55% present in the starting monomer mixture.

TABLE I

RELATIVE F, C, AND —$CF_3$ CONTENT OF PLASMA POLYMERIZED $C_9F_{18}$ MONOMERS. THE RELATIVE F AND C ATOM CONCENTRATIONS WERE COMPUTED FROM DECONVOLUTION OF THE C (1s) XPS PEAK.

| on time/off time (ms) | power (watts) | % F | % C | % O | F/C | % CF3 |
|---|---|---|---|---|---|---|
| | | Pulsed runs | | | | |
| 10/30 | 200 | 53.59 | 45.34 | 1.07 | 1.18 | 15 |
| 10/300 | 200 | 57.92 | 41.53 | 0.55 | 1.39 | 24 |
| 0.1/3 | 100 | 62.90 | 36.60 | 0.50 | 1.72 | 40 |
| | | CW Runs | | | | |
| | 50 | 56.78 | 42.81 | 0.41 | 1.33 | 19 |
| | 5 | 60.78 | 38.40 | 0.82 | 1.58 | 34 |

Figure 4:
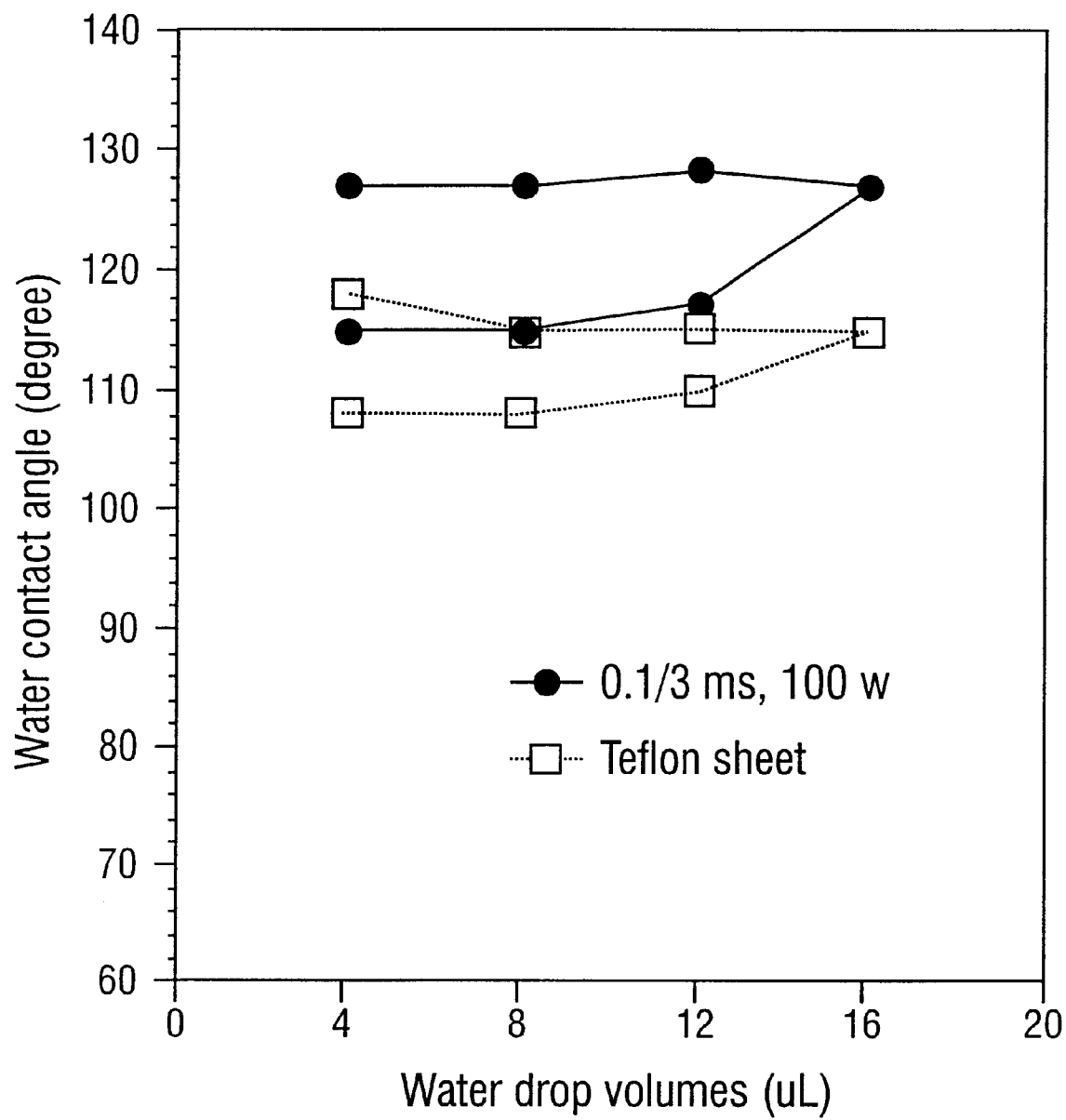
FIG. 4 Comparison of advancing and receding water contact angles for low power pulsed plasma and CW plasma $C_9F_{18}$ synthesized films relative to a Teflon® film standard.
Figure 5:
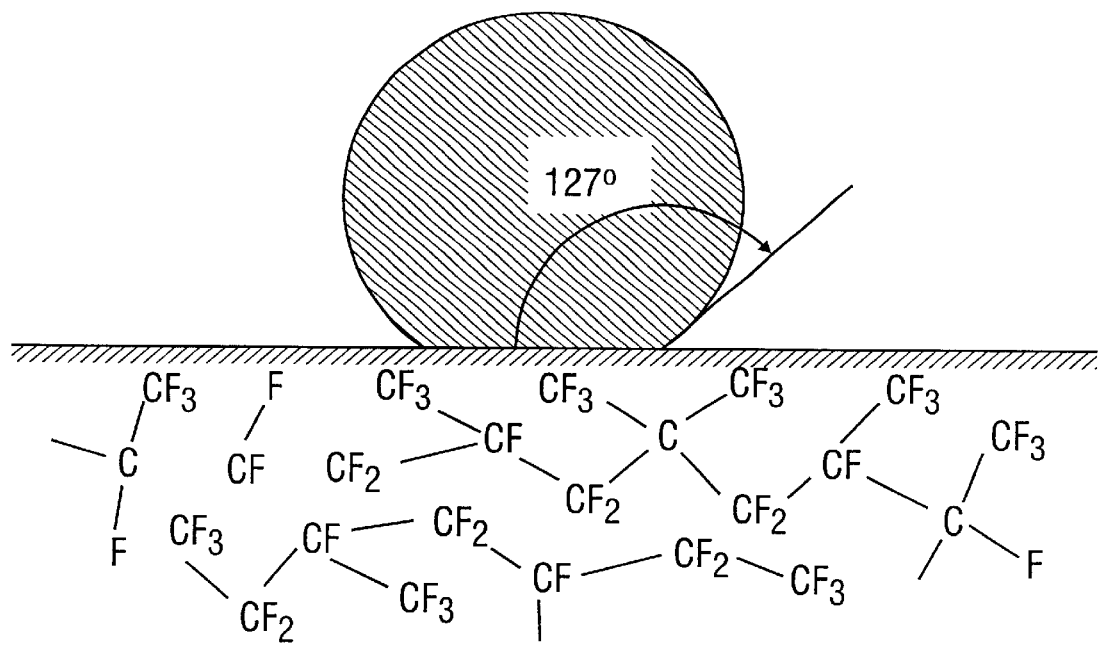
FIG. 5. Illustration showing the non-wettability of a —$CF_3$ dominant surface as produced via low power plasma polymerization of $C_9F_{18}$ monomer.

The hydrophobicities of these unusual fluorocarbon films were evaluated via both advancing ($\theta_a$) and receding ($\theta_r$) water contact angle measurements. Examples of the results obtained are shown in FIG. 4, in which $\theta$ values from a —$CF_3$ dominated films are contrasted with values from a standard Teflon® film (Goodfellow Inc.) sample. The $\theta$ values have an estimated uncertainty of ±3 degrees. As shown in FIG. 4, both the $\theta_a$ and $\theta_r$ values for the 0.1/3 duty cycle pulsed plasma generated films are significantly higher than those obtained for the Teflon® film sample. The 5 watt CW synthesized film exhibited $\theta_a$ values which were slightly less than those of the Teflon® film. Additionally, the $\theta_r$ values for this CW generated film exhibit a slightly higher degree of hysteresis than the other two fluorocarbon samples. The higher $\theta$ values for the pulsed plasma generated films would be in accord with the higher —$CF_3$ content and the higher F/C ratios in this film relative to the 5 watt CW sample (Table I). The inventors also note that the films deposited during the 0.1/3, 100 watt pulsed depositions differ slightly from the lowest power CW runs with respect to the relative concentrations of carbon atoms not bonded directly to fluorine (peaks at 286.5 eV, FIG. 2 and FIG. 3). These particular carbon atoms appear to be slightly more prominent in the CW generated films and this factor may also contribute to the differences in hydrophobicities of these two samples. The differences in these peak intensities may arise from enhanced fluorine atom ablation processes under CW conditions relative to those observed under pulsed operation.

The XPS spectra in FIG. 2 and FIG. 3 confirm that increased destruction of the —$CF_3$ groups is observed under more energetic plasma conditions under both pulsed and CW conditions. This leads to more highly cross-linked film as shown in these figures. This observation is in accord with literature results of previous studies of fluorocarbon films (Yasuda, 1985).

The lowest duty cycle 100 watt pulsed plasma generated film have slightly higher —$CF_3$ content and are more hydrophobic than the lowest wattage CW prepared films. Attempts to generate films at even less energetic conditions, under both pulsed and CW conditions, resulted in the relatively unstable plasmas and/or exceptionally low deposition rates. Conceivably, lower energetic conditions, when coupled with other monomer processes and flow rates, might provide slight enhancements in —$CF_3$ film content. However, the high retention of the monomers' —$CF_3$ groups obtained in the present study indicates there is probably little room for generation of even more hydrophobic films using this particular monomer mixture.

The availability of these extremely hydrophobic fluorocarbon films, with their high —$CF_3$ content, provides a new and more richly fluorinated surface. Significant decreases in plasma protein adsorptions were observed on these —$CF_3$ dominated surfaces, relative to those previously reported for —$CF_2$-structured surfaces. Other important distinctions between the properties of —$CF_3$, relative to conventional —$CF_2$—, surfaces will emerge as comparative studies progress.

Previously, the inventors have reported on film chemistry control during pulsed plasma synthesis of fluorocarbon films (Savage et al., 1991; Panchalingam et al., 1993). In these studies, relatively large scale progressive changes in film compositions were observed with sequential changes in the RF duty cycle employed during plasma polymerization of several perfluorocarbon monomers, all other plasma variables being held constant. These fluorocarbon films exhibited a steady increase in —$CF_2$-functional content as the plasma duty cycle was reduced, resulting in unusually low surface energy films at the lowest duty cycles employed.

This trend towards higher —$CF_2$-film incorporation was demonstrated both with monomers containing high initial —$CF_2$-content (e.g., perfluoro-2-butyl tetrahydrofuran) as well as with monomers having less abundant —$CF_2$-groups (e.g., perfluoropropylene and hexafluoropropylene oxide).

The present invention comprises the first evidence for the controlled plasma synthesis of perfluorocarbon films dominated by —$CF_3$ groups. These exceptionally hydrophobic films were produced by plasma polymerization of a mixture of —$CF_3$ substituted perfluorohexenes [trimer of $C_9F_{18}$ compounds]. This starting isomeric mixture is dominated by —$CF_3$ groups functionalities which account for 55% of the carbons present in these molecules. Additionally, these molecules contain a carbon-carbon double bond useful in helping to promote polymerization, particularly under low energy plasma conditions.

EXAMPLE 10

The same perfluorocarbon substituted trimer mixture noted in Example 9 was mixed with a bromine-containing monomer. Plasma deposition produced a fluorinated film that also contained C—Br reactive surface groups as shown by ESCA analysis.

EXAMPLE 11

Figure 13:
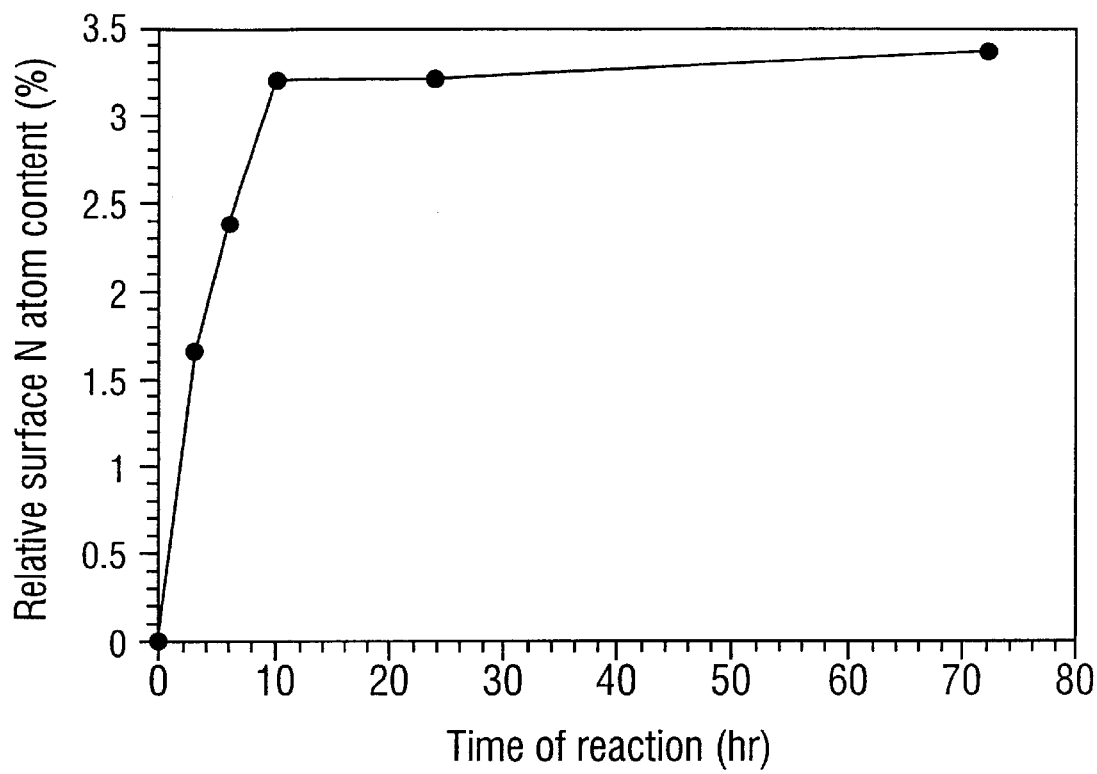
FIG. 13 shows the increased incorporation of surface nitrogen from the covalent reaction of cysteine molecules with an allyl bromide film on a PET substrate as a function of the reaction time between the cysteine solution and the coated PET substrate.

A number of PET substrate surfaces were modified using a pulsed plasma treatment process and allyl bromide monomer, as described previously in Example 1. These samples were employed for a time study of the coupling of cysteine molecules to the surfaces of this C—Br containing substrates. The extent of surface attachment of the cysteine molecules as a function of reaction time was determined by ESCA analysis of the surface N and S content. Reactions were carried out in aqueous solution at pH 7.4 and room temperature. It was observed that the majority of the cysteine attachment to the surface occurred during the first 10 hours of reaction. This result is shown in FIG. 13 which shows the relative surface content of nitrogen atoms as a function of the time of reaction. This result clearly shows the efficiency of the amino acid coupling reaction to the plasma modified surface even where this reaction is carried out at room temperature.

EXAMPLE 12

A pulsed plasma deposition of allyl iodide was employed to provide a surface which contained carbon-iodine (C—I) bonds. As in previous examples, it was observed that the relative surface content of the C—I bonds increased with decreasing energy employed during the deposition step. Subsequently, these C—I containing films were subjected to derivatization reactions utilizing glutamine and cysteine as coupling molecules. It was observed that the amino acids attach to these surfaces as revealed by the presence of N and S via ESCA analysis. However, the amounts of N and S incorporated were less than that observed with the C—Br and C—COCl modified surfaces (Examples 3 and 4, respectively). In a separate experiment a PET modified surface containing plasma deposited C—I groups was immersed in pure $H_2O$ for six hours and that subjected to ESCA analysis. This analysis revealed a decrease in surface I content and increased O content relative to the concentrations before $H_2O$ immersion. This experiment indicates that C—I hydrolysis is occurring during the room temperature immersion experiment and that this hydrolysis process is competitive with the reaction of the C—I groups with the cysteine molecules. Use of more concentrated amino acid solutions and/or lower reaction temperatures would be expected to help promote additional amino acid coupling to the surface and reduced hydrolysis.

EXAMPLE 13

Figure 14:
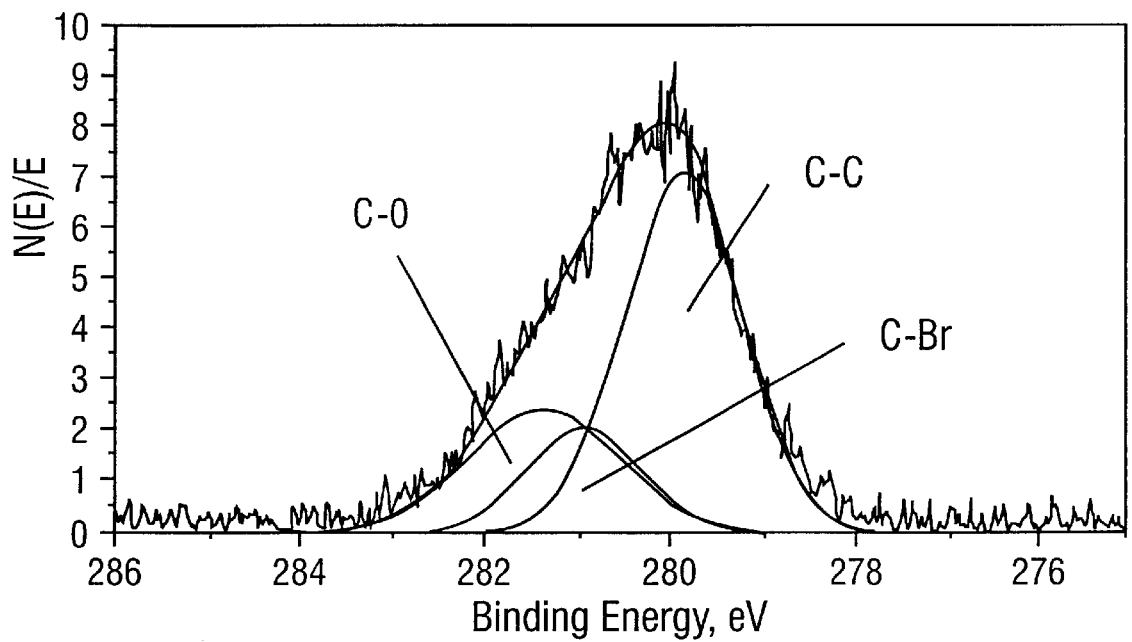
FIG. 14 shows the C(1s) high resolution ESCA spectrum after reaction of a PEO-$NH_2$ polymer (MW=5000) from aqueous solution with an allyl bromide film previously plasma deposited on a PET substrate.

A pulsed plasma surface modification was employed to introduce surface C—Br groups, as described previously in Example 1. This sample was then immersed in an aqueous solution which contained dissolved $NH_2$-PEG-$OCH_3$ polymer molecules. The functionalized PEG polymeric molecules had a nominal molecular weight of 5000 and were purchased from Shearwater Polymers, Inc. After 24 hours of reaction, these PET samples were removed, rinsed with SDS solution and distilled water and then vacuum dried. Subsequent ESCA analysis of these films revealed clearly the surface attachment of the functionalized PEG polymer molecules. The C(1s) high resolution ESCA spectrum obtained after this coupling reaction is shown in FIG. 14. Table II provides a quantitative measure of the surface atom content before and after the derivatization reaction.

TABLE II

ESCA C(1s) Analysis of Surface Atoms on C—Br Modified Surfaces Before and After Attachment of $NH_2$—PEG—$OCH_3$

|  | C | Br | O |
|---|---|---|---|
| Before Derivatization | 0.74 | 0.26 |  |
| After Derivatization | 0.71 | 0.11 | 0.18 |

As shown in both FIG. 14 and Table II there is a substantial oxygen atom presence on the surface after derivatization. The position and binding energy of the C—O ESCA peak identifies this oxygen content as arising form ether groups of the type involved in the PEG linkages. We also note the decrease in surface Br atoms which accompanies attachment of the $NH_2$-PEG-$OCH_3$ molecules, as expected. We also mention explicitly that the N content of the derivatized surfaces is below the ESCA detectability limit as calculated based on the PEG incorporation Subsequently these PET-PEG modified surfaces were employed in protein binding studies using radioactively labeled ($^{125}I$) albumin molecules. A dramatic decrease in albumin surface adsorption (>30 fold decrease) was observed in comparing albumin adsorption on the unmodified PET substrate with that obtained on the PEG modified PET surface. The results obtained clearly support the utility of the surface modification procedure of the present invention to provide a new and convenient approach to manufacturing of non-biologically fouling surfaces.

EXAMPLE 14

A pulsed plasma deposition was employed as generally described in Example 9 to generate a PET modified surface having an extraordinary high surface density of $CF_3$— groups, such as that shown in FIG. 2C containing 40% $CF_3$ groups. This sample was then used to measure protein adsorption (as in Example 13) vis-à-vis that observed on conventional fluorocarbon surfaces. In general, a sharp decrease in protein adsorption was observed on the $CF_3$— dominated films relative to that observed on other fluorocarbon samples. In particular, a two-fold reduction in albumin adsorption was noted on the $CF_3$— dominated surfaces relative to those observed on $CF_2$— dominated (ie., Teflon) surfaces. This example illustrates the utility of the unique $CF_3$— surfaces in reducing non-specific biomolecule adsorptions. Thus, these $CF_3$— surfaces when coupled with an added functional group (such as C—Br as noted earlier) can be employed to reduce non-specific biomolecular adsorptions (e.g., blood platelet adhesion, protein binding, etc.) while simultaneously permitting attachment of specific molecules via the reactive functional groups.

Citations in the following list are incorporated in pertinent part by reference herein.

References

Clark and Shuttlerworth, 1980, *J. Polym. Sci., Polym. Chem. Ed.* 18 27.
Clemence et al., *Bioconjugate Chem.*, 6, 411.
Gsell et al., U.S. Pat. No. 5,258,127, 1993.
Hoffman et al., U.S. Pat. No. 5,055,316, 1991.
Massia et al., 1991, *J Biomedical Materials Research*, 25, 223.
Miyamoto et al., U.S. Pat. No. 5,178,962, 1993.
Panchalingam et al., 1993, *J. Biomater. Sci.*, 5, 131.
Panchalingam et al., 1994, *J. Appl. Polymer. Sci.; Appl. Polymer Symposium*, 54, 123.
Ranieri et al. [*Int. J. Developmental Neuroscience*, 12, 725 (1994).
Savage et al., 1991, *Chemistry of Materials*, 3, 575.
Sigrist et al., *Optical Engineering*, August, 1994 34(8), 2339.
Yasuda, 1986, *Plasma Polymerization*, P. 182, Academic Press, NY.

Those skilled in the art will perceive many equivalents of the procedures, active group-containing monomers, perfluorinated compounds and surfaces specified in the following claims.

What is claimed is:

1. A solid surface having pendant perfluorinated groups where the $CF_3/CF_2$ carbon ratio range from about 1.2 to about 3.2.

2. The solid surface of claim 1 where the $CF_3$ is at least 15 to 40% of the total carbon present.

3. A surface having a pendant perfluorinated carbonaceous compound and a water contact angle greater than about 120 degrees, wherein said pendant perfluorinated carbonaceous compound has a $CF_3/CF_2$ carbon ratio ranging from about 1.2 to about 3.2.

4. The surface of claim 3 where the perfluorinated carbonaceous compound is $CF_3$ substituted perfluorinated hexene.

* * * * *

UNITED STATES PATENT AND TRADEMARK OFFICE
CERTIFICATE OF CORRECTION

PATENT NO. : 6,306,506 B1  
APPLICATION NO. : 09/231391  
DATED : October 23, 2001  
INVENTOR(S) : Richard B. Timmons and Jenn-Hann Wang It is certified that error appears in the above-identified patent and that said Letters Patent is hereby corrected as shown below:

In the Specification

At Col. 1, line 5, delete

"The U.S. Government has certain rights in the present invention pursuant to the National Institutes of Health under Grant #R01AR43186-01 and by the Texas Higher Education Coordinating Board ATP Program under Grant #003656-105."

At Col. 1, line 5, add

--This invention was made with U.S. Government support under Grant #R01AR43186-01 awarded by the National Institutes of Health and under Grant #003656-105 awarded by the Texas Higher Education Coordinating Board ATP Program. The government has certain rights in this invention.--

Signed and Sealed this
Twelfth Day of August, 2014

Michelle K. Lee
*Deputy Director of the United States Patent and Trademark Office*